US 11,324,450 B2

(12) United States Patent
Joe et al.

(10) Patent No.: US 11,324,450 B2
(45) Date of Patent: May 10, 2022

(54) METHOD, ELECTRONIC DEVICE, AND STORAGE MEDIUM FOR DETECTING BIOMETRIC INFORMATION

(71) Applicant: Samsung Electronics Co., Ltd., Suwon-si (KR)

(72) Inventors: Daniel Joe, Suwon-si (KR); Minhyun Cho, Suwon-si (KR); Seyong Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 307 days.

(21) Appl. No.: 16/684,537

(22) Filed: Nov. 14, 2019

(65) Prior Publication Data

US 2020/0146630 A1 May 14, 2020

(30) Foreign Application Priority Data

Nov. 14, 2018 (KR) .......................... 10-2018-0139626

(51) Int. Cl.
*A61B 5/00* (2006.01)
*H04W 4/38* (2018.01)
(Continued)

(52) U.S. Cl.
CPC .......... *A61B 5/6844* (2013.01); *A61B 5/0004* (2013.01); *A61B 5/02433* (2013.01);
(Continued)

(58) Field of Classification Search
None
See application file for complete search history.

(56) References Cited

U.S. PATENT DOCUMENTS

| 7,527,596 B2 | 5/2009 | Ghigini |
| 2016/0255944 A1* | 9/2016 | Baranski .................. A44C 5/20 |

(Continued)

FOREIGN PATENT DOCUMENTS

| JP | 2004-254882 A | 9/2004 |
| JP | 2008-528151 A | 7/2008 |

(Continued)

OTHER PUBLICATIONS

Yuki Matsuda et al., "WaistonBelt 2: A Belt-type Wearable Device for Monitoring Abdominal Circumference, Posture and Activity", 2016 Ninth International Conference on Mobile Computing and Ubiquitous Networking (ICMU), Oct. 4-6, 2016, 6 pages.

(Continued)

*Primary Examiner* — Curtis A Kuntz
*Assistant Examiner* — Jerold B Murphy

(57) ABSTRACT

An electronic device may include: a housing; a display configured to be viewed through a first portion of the housing; a photoplethysmogram sensor exposed through a second portion of the housing and configured to measure a biometric signal from a body part of a user while being in contact with the body part of the user; a fastening structure connected to the housing and configured to be attached to the body part of the user; a wireless communication circuit; a processor provided inside the housing and operatively connected to the display, the photoplethysmogram sensor, and the wireless communication circuit; and a memory operatively connected to the processor. The memory stores instructions, when executed, to allow the processor to: receive data from the photoplethysmogram sensor; determine a first parameter; determine a distance between the body part of the user and the fastening structure; and provide user guidance information on the display.

19 Claims, 18 Drawing Sheets

(51) Int. Cl.
    *H04B 1/3827* (2015.01)
    *A61B 5/024* (2006.01)
    *H04W 84/18* (2009.01)

(52) U.S. Cl.
    CPC .......... *A61B 5/02438* (2013.01); *A61B 5/684* (2013.01); *A61B 5/742* (2013.01); *H04B 1/385* (2013.01); *H04W 4/38* (2018.02); *A61B 2562/0219* (2013.01); *A61B 2562/0238* (2013.01); *H04W 84/18* (2013.01)

(56) References Cited

U.S. PATENT DOCUMENTS

| | | |
|---|---|---|
| 2016/0278704 A1 | 9/2016 | Park et al. |
| 2018/0271431 A1* | 9/2018 | Lee ................. A61B 5/444 |
| 2020/0146629 A1* | 5/2020 | Sun ................. A61B 5/0205 |

FOREIGN PATENT DOCUMENTS

| | | |
|---|---|---|
| JP | 2010-029458 A | 2/2010 |
| KR | 10-1784484 B1 | 10/2017 |

OTHER PUBLICATIONS

X F Teng et al., "The effect of contacting force on photoplethysmographic signals", Physiological Measurement, Aug. 11, 2004, 14 pages.

International Search Report dated Feb. 11, 2020 in connection with International Patent Application No. PCT/KR2019/014924, 3 pages.

Written Opinion of the International Searching Authority dated Feb. 11, 2020 in connection with International Patent Application No. PCT/KR2019/014924, 5 pages.

* cited by examiner

METHOD, ELECTRONIC DEVICE, AND STORAGE MEDIUM FOR DETECTING BIOMETRIC INFORMATION

CROSS-REFERENCE TO RELATED APPLICATIONS

This application is based on and claims priority under 35 U.S.C. 119 to Korean Patent Application No. 10-2018-0139626 filed on Nov. 14, 2018 in the Korean Intellectual Property Office, the disclosure of which is herein incorporated by reference in its entirety.

BACKGROUND

1. Field

Various embodiments relate to a method, an electronic device, and a storage medium for detecting biometric information.

2. Description of Related Art

Electronic devices, such as wearable electronic devices, smartphones, and the like, may be equipped with sensors capable of measuring biometric signals, and may provide a user with a variety of biometric information using the sensors. For example, the sensor capable of measuring a biometric signal may be a photoplethysmography (PPG) sensor based on a multi-color light-emitting diode (LED). For example, the electronic device may include a PPG sensor, and may measure PPG signals (also, referred to as "PPG data" or "biometric signals") using the PPG sensor, thereby providing the user with biometric information such as a heart rate (HR), breathing information, stress levels, blood pressure (BP), a blood flow rate, and/or circulatory status of the user.

SUMMARY

For the implementation of wearable electronic device-based healthcare services, electronic devices are required to detect a variety of biometric information, such as saturation of percutaneous oxygen (SpO2), blood pressure, and/or blood sugar, as well as a heart rate. To this end, a method of measuring a biometric signal using a PPG sensor with accuracy improved over the conventional method is required.

In order to improve the accuracy of measurement of a biometric signal, a correctly measured posture of the user is required, and the wearing state of an electronic device on the user's body should be optimized such that the PPG sensor of the electronic device and the users body come into optimal contact with each other. However, in the prior art, there is no technique for providing wearing guidance of an electronic device in order to optimize the degree of contact between the PPG sensor of the electronic device and the users body.

An existing wearable electronic device capable of measuring biometric signals cannot determine whether or not the user is wearing the electronic device in a manner such that the degree of contact between the PPG sensor of the electronic device and the users body is optimized because the criteria for determining whether or not the electronic device is optimally worn on a body part of the user are ambiguous even if the electronic device is properly worn on the body part of the user. For example, if the electronic device worn on the body part of the user is excessively tight, the electronic device cannot determine this wearing state, which causes a problem in which the users biomedical signal is distorted relative to an actual normal signal.

Various embodiments may provide a method, an electronic device, and a storage medium for providing guidance for wearing an electronic device on the body in order for the electronic device to detect accurate biometric information. For example, the electronic device may provide the user with information that allows the user to adjust the degree of contact between the electronic device and the user's body in order for the PPG sensor to accurately measure biometric signals.

Various embodiments may provide a method, an electronic device, and a storage medium for automatically adjusting the degree of contact between the electronic device and the users body in order to accurately detect biometric information, thereby maximizing the accuracy and consistency of measurement of biometric signals. For example, the electronic device may analyze the biometric signals measured by the PPG sensor and may automatically adjust the degree of contact between the electronic device and the users body to the wearing state in which biometric information can be accurately detected instead of merely tightening the PPG sensor on the body.

According to various embodiments, an electronic device may include: a housing; a display configured to be viewed through a first portion of the housing; a photoplethysmogram (PPG) sensor exposed through a second portion of the housing and configured to measure a biometric signal from a body part of a user while being in contact with the body part of the user; a fastening structure connected to a portion of the housing and configured to be attached to the body part of the user; a wireless communication circuit; a processor provided inside the housing and operatively connected to the display, the photoplethysmogram sensor, and the wireless communication circuit; and a memory operatively connected to the processor, wherein the memory stores instructions, when executed, to allow the processor to: receive data from the photoplethysmogram sensor; based at least in part on the received data, determine a first parameter; based at least in part on the determined first parameter, determine a distance between the body part of the user and the fastening structure; and based at least in part on the distance, provide user guidance information on the display.

According to various embodiments, a method for detecting biometric information in an electronic device may include: receiving data from a photoplethysmogram sensor of the electronic device; based at least in part on the received data, determining a first parameter; based at least in part on the determined first parameter, determining a distance between a body part of the user and a fastening structure of the electronic device; and based at least in part on the distance, providing user guidance information on the display of the electronic device.

According to various embodiments, a storage medium may include instructions that, when executed by at least one circuit, allow the at least one circuit to perform one or more operations of: receiving data from a photoplethysmogram sensor of the electronic device; based at least in part on the received data, determining a first parameter; based at least in part on the determined first parameter, determining a distance between a body part of the user and a fastening structure of the electronic device; and based at least in part on the distance, providing user guidance information on the display of the electronic device.

A method, an electronic device, and a storage medium for detecting biometric information according to various embodiments can provide techniques for improving the accuracy of measurement of biometric signals of the electronic device. For example, the electronic device can determine the contact state between a PPG sensor of the electronic device and a users skin to maintain an appropriate contact state, thereby enabling the electronic device to acquire a high-quality biometric signal. For example, the electronic device can be self-controlled to maintain an appropriate contact state between the electronic device and the users skin at all times, periodically or at a specific time. Thus, it is possible to minimize distortion of a biometric signal and deterioration of the performance of the electronic device due to various variables, such as the posture of the user and/or the wearing state of the electronic device when the electronic device measures the biometric signal. Techniques for improving the accuracy of measurement of the biometric signal can be applied to various mobile electronic devices, such as smartphones and/or wearable electronic devices, thereby improving the reliability of personalized mobile healthcare services by obtaining high-quality biometric signals.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 15C, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
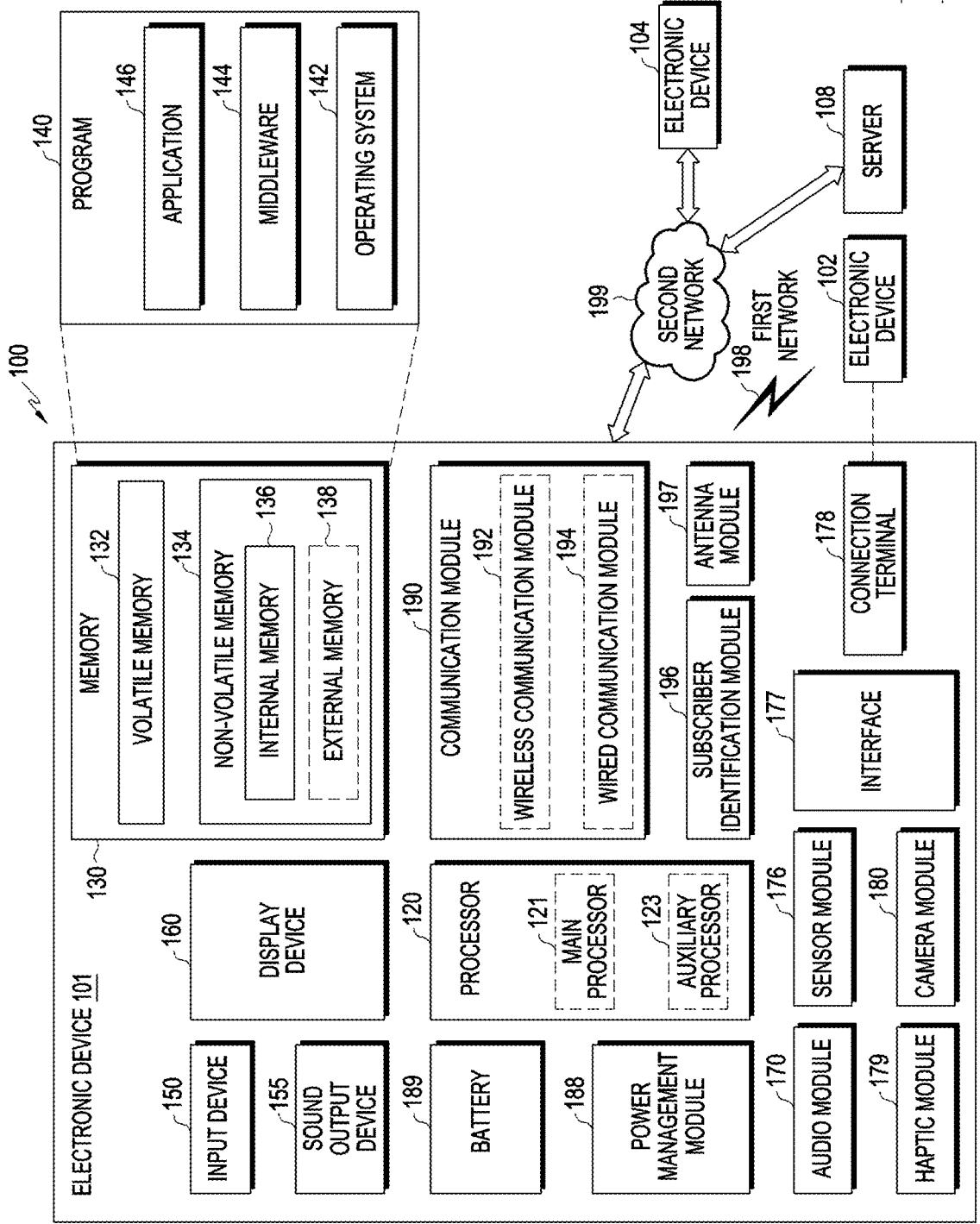
FIG. 1 illustrates a block diagram of an electronic device in a network environment according to various embodiments.

FIG. 1 illustrates a block diagram of an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, a memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wired) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wired) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his or her tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
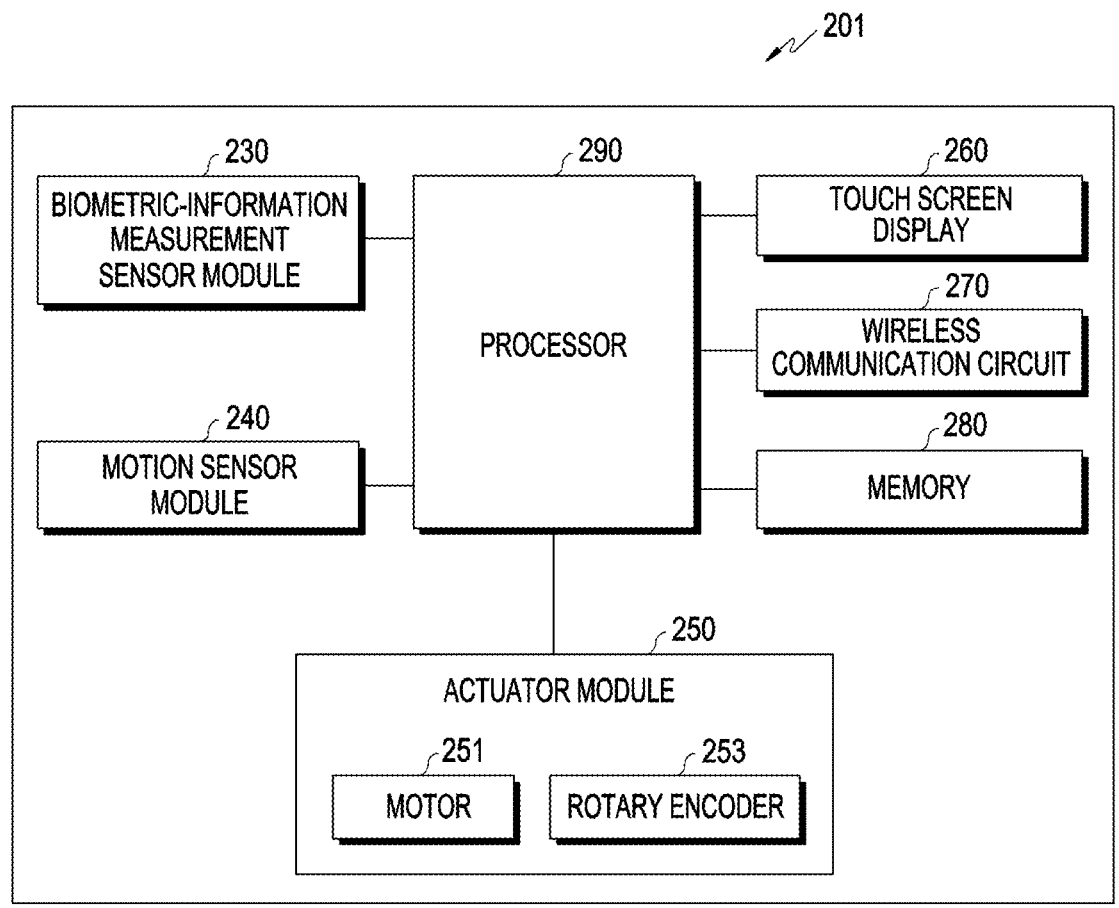
FIG. 2 illustrates a block diagram of an electronic device according to various embodiments.

FIG. 2 illustrates a block diagram of an electronic device 201 (e.g., the electronic device 101) according to various embodiments.

Referring to FIG. 2, the electronic device 201 may include a biometric-information measurement sensor module 230, a motion sensor module 240, an actuator module 250, a touch screen display 260, a wireless communication circuit 270, a memory 280, and a processor 290.

According to an embodiment, the biometric-information measurement sensor module 230 may be the biometric sensor of the sensor module 176 in FIG. 1.

For example, the biometric-information measurement sensor module 230 may include a photoplethysmogram (PPG) sensor configured to measure blood pressure from a body part of a user. For example, the PPG sensor may be the PPG sensor 301 in FIG. 3.

Figure 3:
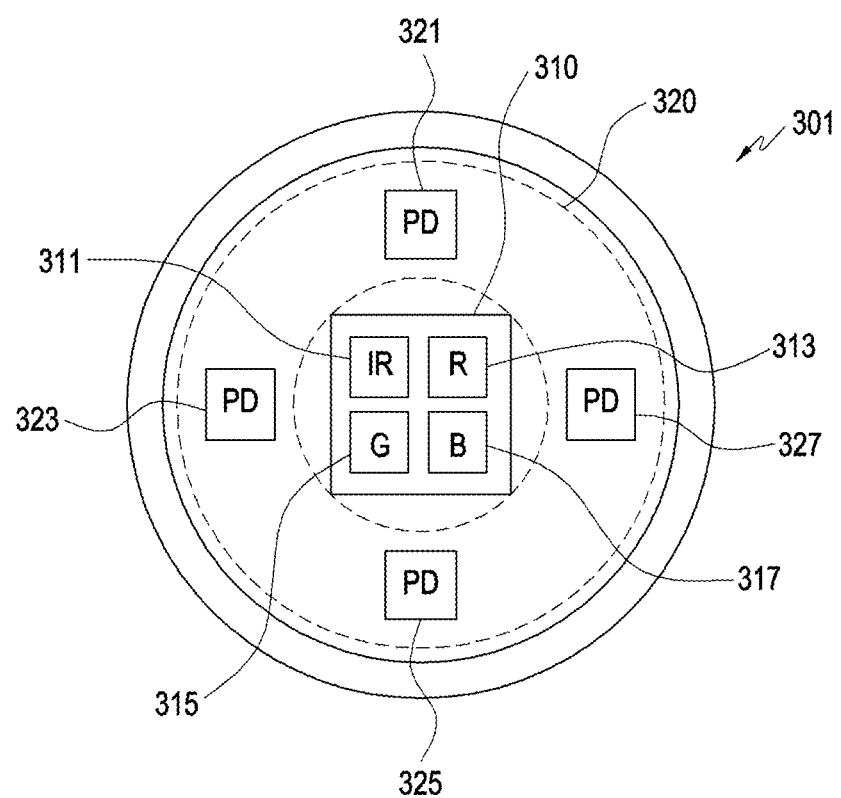
FIG. 3 illustrates a diagram of a PPG sensor according to various embodiments.

FIG. 3 shows a PPG sensor according to various embodiments.

Referring to FIG. 3, a PPG sensor 301 may include a light-emitting module 310 and a light-receiving module 320. The light-emitting module 310 may include a multi-color light-emitting diode (LED), and may include an infrared ray (IR) LED 311 (wavelength (λc)=950 (±10) nm), a red LED 313 (λc=660 (±10) nm), a green LED 315 (λc=525 (±10) nm), and/or a blue LED 317 (λc=460 nm). The light-receiving module 320 may include one or more photodiodes (PDs) 321, 323, 325, and 327.

For example, the processor 290 may determine biometric information of the user, based on biometric signals measured using the biometric-information measurement sensor module 230. For example, the processor 290 may measure a PPG signal using the PPG sensor of the biometric-information measurement sensor module 230, and, based on the measured PPG signal, may determine the biometric information of the user. For example, the biometric information may include information about a heart rate, oxygen saturation, blood pressure, and/or blood glucose.

According to an embodiment, the motion sensor module 240 may include the acceleration sensor and/or the gyro sensor of the sensor module 176 in FIG. 1.

For example, the processor 290 may monitor the current motion of the user, or may determine the state thereof using the motion sensor module 240.

For example, when measuring a biometric signal of the user, the processor 290 may identify whether or not the electronic device 201 is provided on a predetermined body part of the user (e.g., on the wrist) using a value measured by the motion sensor module 240. For example, the processor 290 may compare an acceleration value measured using the acceleration sensor of the motion sensor module 240 with a specified reference acceleration range (or a reference acceleration value), thereby determining whether or not the electronic device 201 is provided on a predetermined body part of the user. For example, if the measured acceleration value is included in the reference acceleration range, the processor 290 may determine that electronic device 201 is provided on a predetermined body part of the user. For example, the reference acceleration range may be determined based on one or more acceleration values measured by the electronic device 201 using the acceleration sensor of the motion sensor module 240 in the state in which the electronic device 201 is provided on a predetermined body part of the user, and may be stored in the memory 280.

According to an embodiment, the actuator module 250 may include a motor 251 and a rotary encoder 253. For example, the motor 251 may include a thin electric motor in the form of a pancake.

For example, the processor 290 may adjust the distance between fasteners (e.g., a first fastener 450 and a second fastener 460) (also, referred to as "straps") of the electronic device 201 and a body part of the user using the motor 251.

For example, the fasteners may be configured so as to attach and detach the electronic device 201 to and from a body part of the user (e.g., a wrist and/or an ankle).

For example, the processor 290 may adjust the degree of tightening of the fasteners of the electronic device 201 with respect to a body part of the user using the motor 251, and may also adjust the degree of contact between the electronic device 201 and a users skin.

For example, the processor 290 may measure the rotational angle of the motor 251 using the rotary encoder 253, and, based on the measured rotational angle, may obtain the distance between the fasteners of the electronic device 201 and a body part of the user (obtain the degree of tightening of the fasteners of the electronic device 201 with respect to a body part of the user).

According to an embodiment, the touch screen display 260 may be the display 160 in FIG. 1. For example, the processor 290 may enable the touch screen display 260 to display biometric information of the user, which is identified using the biometric-information measurement sensor module 230. For example, the processor 290 may enable the touch screen display 260 to display user guidance information of the electronic device 201.

For example, the user guidance information may include information that guides the user to adjust the distance between the electronic device 201 and a body part of the user in order to measure optimal biometric signals of the user using the biometric-information measurement sensor module 230.

According to an embodiment, the wireless communication circuit 270 may be the communication module 190 in FIG. 1. For example, the wireless communication circuit 270 may include a cellular module, a Wi-Fi module, a Bluetooth (BT/BLE) module, and/or an NFC module. For example, the processor 290 of the electronic device 201 may be paired with other peripheral electronic devices using the wireless communication circuit 270 and may transmit and receive data to and from other peripheral electronic devices.

According to an embodiment, the memory 280 may be the memory 130 in FIG. 1.

For example, the memory 280 may store information about the distance between the electronic device 201 and a body part of the user (e.g., the degree of contact between the electronic device and the users s kin and/or the degree of tightening of the fasteners), which is identified using the actuator module 250.

The memory 280 may store biometric information of the user identified using the biometric-information measurement sensor module 230. For example, the biometric information may include information about a heart rate, oxygen saturation, blood pressure, and/or blood glucose.

According to an embodiment, the processor 290 may be the processor 120 in FIG. 1.

For example, the processor 290 may control at least one element of the electronic device 201 (e.g., the biometric-information measurement sensor module 230, the motion sensor module 240, the actuator module 250, the touch screen display 260, the wireless communication circuit 270, or the memory 280).

For example, the processor 290 may identify biometric information of the user, based on a specified algorithm, using the users biometric signal obtained through the biometric-information measurement sensor module 230. For example, in order to adjust the gap between the electronic device 201 and a body part of the user, the processor 290 may obtain and determine the degree of tightening of the fasteners of the electronic device 201 with respect to the body part of the user in the form of a feedback system, based on measurement values of the biometric-information measurement sensor module 230 and the motion sensor module 240.

Figure 4:
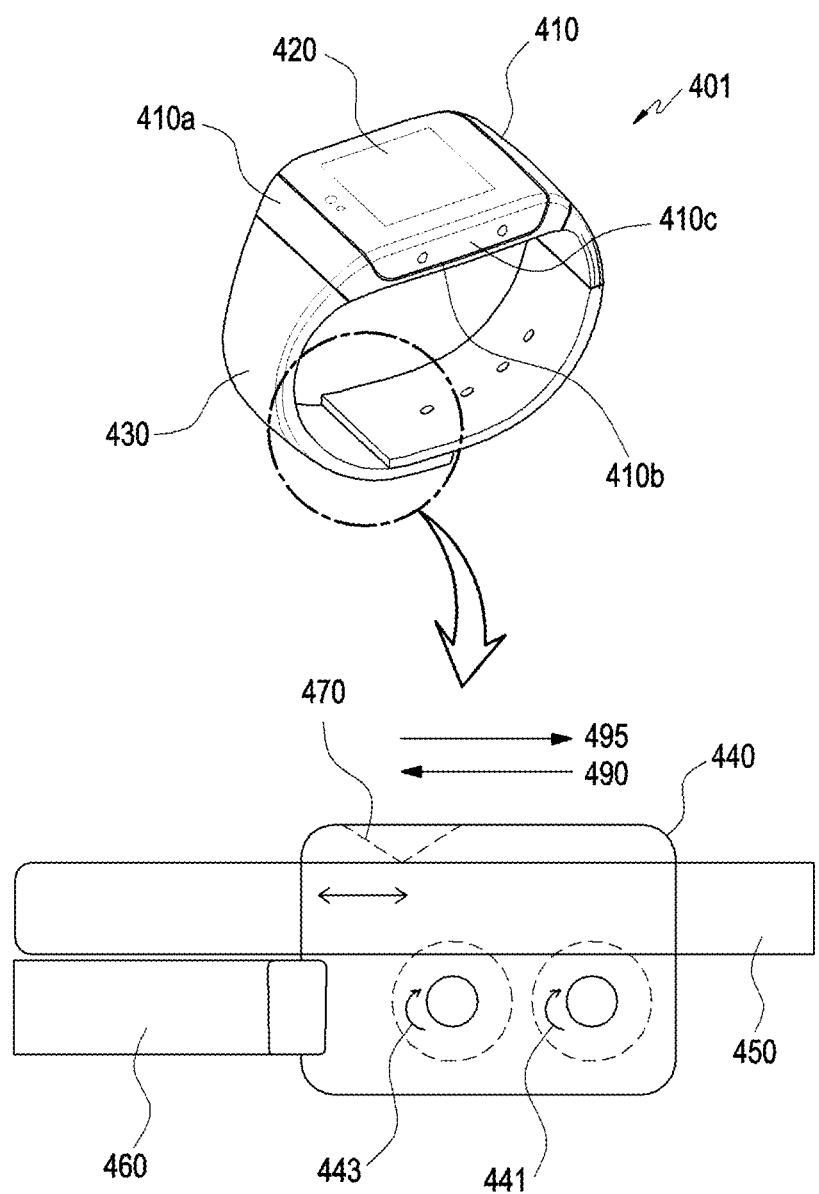
FIG. 4 illustrates a diagram of an electronic device according to various embodiments.

FIG. 4 illustrates a diagram of an electronic device 401 (e.g., the electronic device 101 and/or the electronic device 201) according to various embodiments.

Referring to FIG. 4, the electronic device 401 may be a wearable electronic device in a watch or band form. For example, the electronic device 401 may include a housing 410, a touch screen display 420 (e.g., the touch screen display 260), and a fastening structure 430.

According to an embodiment, the housing 410 may include a first portion 410a, a second portion 410b, and a side surface 410c that surrounds the space between the first portion 410a and the second portion 410b. The touch screen display 420 may be viewed through the first portion 410a of the housing 410. Although not shown in the drawing, a PPG sensor (e.g., the biometric-information measurement sensor module 230) may be exposed through the second portion 410b of the housing 410.

According to an embodiment, the fastening structure 430 may be coupled to a portion of the housing 410 and may be configured to be attached to a body part of the user (e.g., a wrist, an ankle, etc.).

For example, the fastening structure 430 may include an actuator module 440 (e.g., the actuator module 250), a first fastener 450, and a second fastener 460, and the first fastener 450 and the second fastener 460 may be referred to as "straps".

For example, the first fastener 450 and the second fastener 460 may be made of any of various materials and in any of various shapes. For example, the first fastener 450 and the second fastener 460 may be made of a woven material, leather, rubber, urethane, metal, ceramic, or a combination thereof. For example, the first fastener 450 and the second fastener 460 may be configured to be attached to and detached from a body part of the user, and the length thereof may be adjusted within an effective length by the actuator module 440.

For example, the actuator module 440 may include a motor 441 (e.g., the motor 251) and a rotary encoder 443 (e.g., the rotary encoder 253).

For example, the distance between the electronic device 401 and a body part of the user may be automatically adjusted by the motor 441.

For example, the first fastener 450 may be coupled to the second fastener 460, and may be moved in a first direction 490 or a second direction 495 according to the operation of the motor 441. For example, the degree of tightening of the electronic device 401, which is worn on a body part of the user, with respect to the body part of the user may be automatically adjusted according to the movement of the first fastener 450 while the second fastener 460 is fixed. Therefore, it is possible to automatically adjust the distance between the electronic device 401 and the body part of the user (i.e., the degree of contact between the electronic device 401 and a users skin). For example, if the first fastener 450 is moved in the first direction 490, the electronic device 401 may be adjusted so as to be tightly worn on the users wrist, thereby performing adjustment to reduce the distance between the electronic device 401 and the body part of the user. For example, if the first fastener 450 is moved in the second direction 495, the electronic device 401 may be adjusted so as to be loosely worn on the users wrist, thereby performing adjustment to increase the distance between the electronic device 401 and the body part of the user.

For example, the rotary encoder 443 may measure the rotational angle of the motor 441, and the electronic device 401 may obtain degree of tightening of the fasteners 450 and 460 with respect to the user's body, based on the measurement of the rotational angle. For example, a leaf spring 470 may be provided to the actuator module 440, and the leaf spring 470 may prevent the fasteners 450 and 460 from unintentionally slipping down or loosening.

Although the embodiments in FIGS. 2 and 4 describe that the electronic device (e.g., the electronic device 101, the processor 120 of the electronic device 101, the electronic device 201, the processor 290 of the electronic device 201, and/or the electronic device 401) adjusts the distance between the electronic device and a body part of the user by adjusting the degree of tightening of the fasteners (e.g., the first fastener 450 and the second fastener 460) of the electronic device with respect to a body of the user using the motor (e.g., the motor 251 or the motor 441), the electronic device may adjust the distance between the electronic device and a body part of the user by other methods. For example, the electronic device may be configured to automatically perform adjustment to increase or reduce the volume of the housing (e.g., a portion (e.g., the second portion 410b) of the housing 410) of the electronic device, thereby allowing the distance between the electronic device and a body part of the user to be increased or reduced.

According to various embodiments, an electronic device (e.g., the electronic device 101, the electronic device 201, or the electronic device 401) may include: a housing (e.g., the housing 410); a touch screen display (e.g., the display device 160 or the touch screen display 260) configured to be viewed through a first portion of the housing; a photoplethysmogram (PPG) sensor (e.g., the biometric-information measurement sensor module 230 or the PPG sensor 301) exposed through a second portion (e.g., the second portion 410a) of the housing and configured to measure a biometric signal from a body part of a user while being in contact with the body part; a fastening structure (e.g., the fastening structure 430) connected to a portion of the housing and configured to be attached to the body part of the user; a wireless communication circuit (e.g., the communication module 190 or the wireless communication circuit 270) provided inside the housing; a processor (e.g., the processor 120 or the processor 290) provided inside the housing and operatively connected to the touch screen display, the photoplethysmogram sensor, and the wireless communication circuit; and a memory (e.g., the memory 130 or the memory 280) operatively connected to the processor, wherein the memory may store instructions, when executed, to allow the processor to: receive data from the photoplethysmogram sensor; based at least in part on the received data, determine a first parameter; based at least in part on the determined first parameter, determine a distance between the body part of the user and the fastening structure; and based at least in part on the distance, provide user guidance information on the display.

According to various embodiments, the instructions may allow the processor to, based at least in part on the received data, determine a second parameter, and, based at least in part on the determined first parameter and the second parameter, determine the distance.

According to various embodiments, the instructions may allow the processor to, based at least in part on a ratio of the determined first parameter to second parameter, determine the distance.

According to various embodiments, the photoplethysmogram sensor may include a light-receiving module that includes at least one light-emitting diode (LED) (e.g., the IR LED 311, the red LED 313, the green LED 315, and/or the blue LED 317) and at least one photodiode (e.g., one or more photodiodes 321, 323, 325, and 327), the first parameter may include information on the amount of light that is emitted from the LED, passes through a blood vessel of the user, and is reflected thereby to then be received by the light-receiving module, and the second parameter may include information on the amount of light that is emitted from the LED, passes through a living tissue other than the blood vessel of the user, and is reflected thereby to then be received by the light-receiving module.

According to various embodiments, the fastening structure may further include an actuator module (e.g., the actuator module 440), and the instructions may allow the processor to, based at least in part on the determined first parameter, adjust the distance between the body part and the fastening structure using the actuator module.

According to various embodiments, the electronic device may be a wearable device.

According to various embodiments, the instructions may allow the processor to, if the distance is greater than a reference distance stored in the memory, performing adjustment to reduce the distance between the body part and the fastening structure by a specified reference value using the actuator module.

According to various embodiments, the instructions may allow the processor to, if the distance is less than a reference distance stored in the memory, perform adjustment to increase the distance between the body part and the fastening structure by a specified reference value using the actuator module.

According to various embodiments, the electronic device may further include a motion sensor module (e.g., the motion sensor module 240), and the instructions may allow the processor to, obtain at least one acceleration value through the motion sensor module, and, based at least in part on the obtained acceleration value, provide user guidance information indicating a specified wearing position of the electronic device on the touch screen display.

According to various embodiments, the photoplethysmogram sensor may further include at least one infrared light-emitting diode, and the instructions may allow the processor to, receive data from the at least one infrared light-emitting diode, and, based at least in part on the received data, identify that the electronic device is in contact with the body part of the user.

According to various embodiments, the electronic device may further include a sensor module (e.g., the sensor module 176) wherein the instructions may allow the processor to, based on at least one piece of schedule information stored in the memory, location information of the electronic device obtained through the sensor module, acceleration information of the electronic device obtained through the sensor module, or current time information, identify status information of the electronic device, and, based at least in part on the status information of the electronic device, activate the photoplethysmogram sensor.

According to various embodiments, an electronic device (e.g., the electronic device 101, the electronic device 201, or the electronic device 401) may include: a housing (e.g., the housing 410); a touch screen display (e.g., display device 160 or the touch screen display 260) configured to be viewed through a first portion of the housing; a photoplethysmogram (PPG) sensor (e.g., the biometric-information measurement sensor module 230 or the PPG sensor 301) exposed through a second portion (e.g., the second portion 410a) of the housing and configured to measure a biometric signal from a body part of a user while being in contact with the body part; a fastening structure (e.g., the fastening structure 430) connected to a portion of the housing and configured to be attached to the body part of the user; a wireless communication circuit (e.g., the communication module 190 or the wireless communication circuit 270) provided inside the housing; a processor (e.g., the processor 120 or the processor 290) provided inside the housing and operatively connected to the display, the photoplethysmogram sensor, and the wireless communication circuit; and a memory (e.g., the memory 130 or the memory 280) operatively connected to the processor, wherein the memory may store instructions that, when executed, allow the processor to: receive data from the photoplethysmogram sensor; based at least in part on the received data, determine a first parameter; based at least in part on the determined first parameter, determine a degree of contact between the body part of the user and the fastening structure; and based at least in part on the degree of contact, provide user guidance information on the display.

According to various embodiments, the instructions may allow the processor to determine the degree of contact according to at least one of a distance between the body part of the user and the fastening structure or a pressure applied to the portion of the body of the user by the fastening structure.

Figure 5:
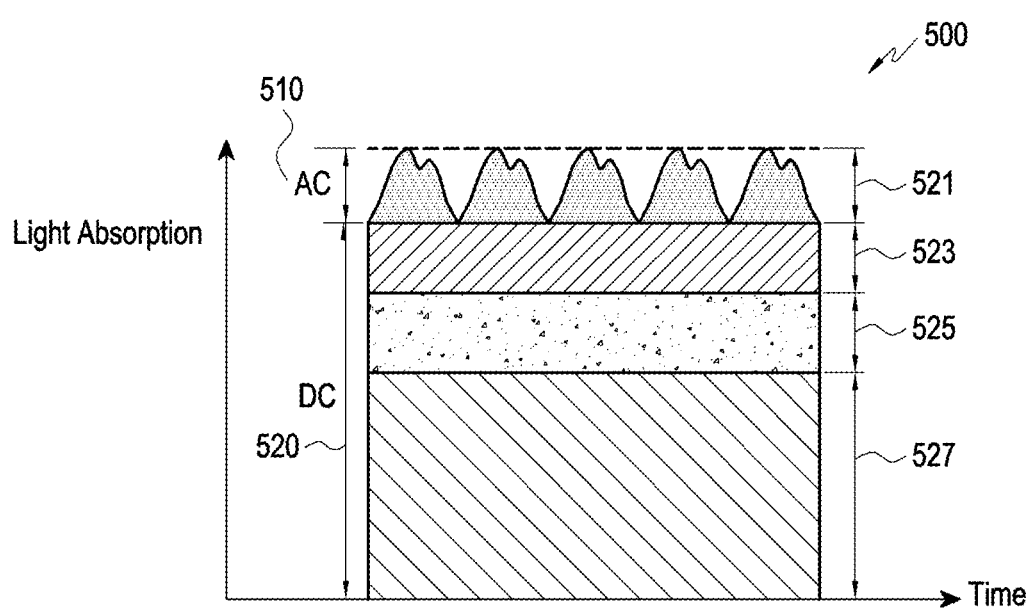
FIG. 5 illustrates a diagram for explaining a PPG signal measured through a PPG sensor of an electronic device according to various embodiments.

FIG. 5 illustrates a diagram for explaining a PPG signal measured through a PPG sensor (e.g., the biometric-information measurement sensor module 230 and/or the PPG sensor 301) of an electronic device (e.g., the electronic device 101, the electronic device 201, and/or the electronic device 401) according to various embodiments.

Referring to FIG. 5, a PPG signal may include an alternating current (AC) signal value and a direct current (DC) signal value.

For example, when at least one LED of the PPG sensor emits light, some light may reach the users arterial blood, venous blood, bones, and/or skin tissue (e.g. epidermis and/or dermis).

For example, a portion 521 of the light reaching the arterial blood may be changed and absorbed due to a change in the arterial blood volume according to a users pulse, and some of the light may constitute an AC signal 510. The value of the AC signal 510 may indicate the difference between a systolic blood flow rate and a diastolic blood flow rate.

For example, some of the light 523 reaching and absorbed by the diastolic arterial blood, the light 525 reaching and absorbed by the venous blood, the light 527 reaching and absorbed by the skin tissue (e.g., the epidermis and/or the dermis), and/or the light reaching and absorbed by the bones may constitute DC signals 520. For example, the value of the DC signal 520 is used to normalize the value of the AC signal 510, and may be affected little by the contraction and relaxation of the blood vessel.

Figure 6A:
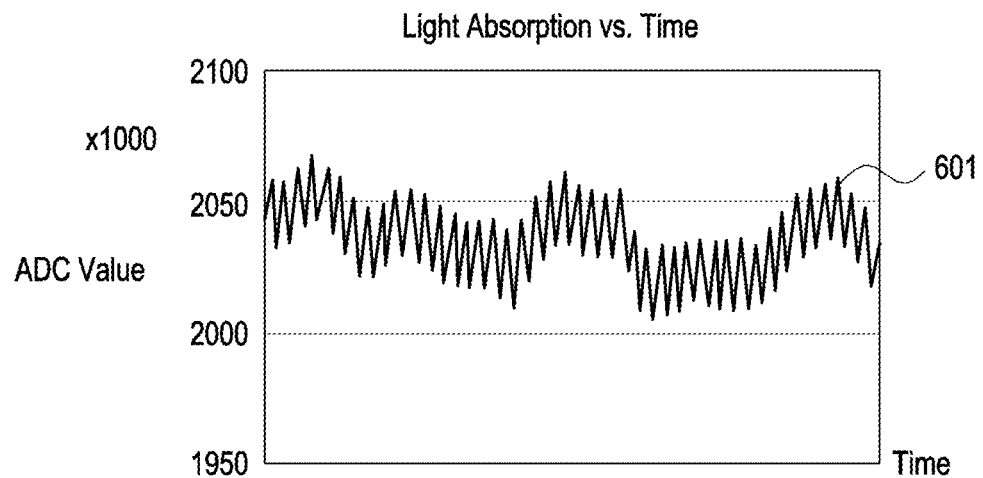
FIG. 6A illustrates a diagram of a PPG signal measured through a PPG sensor of an electronic device according to various embodiments.
Figure 6B:
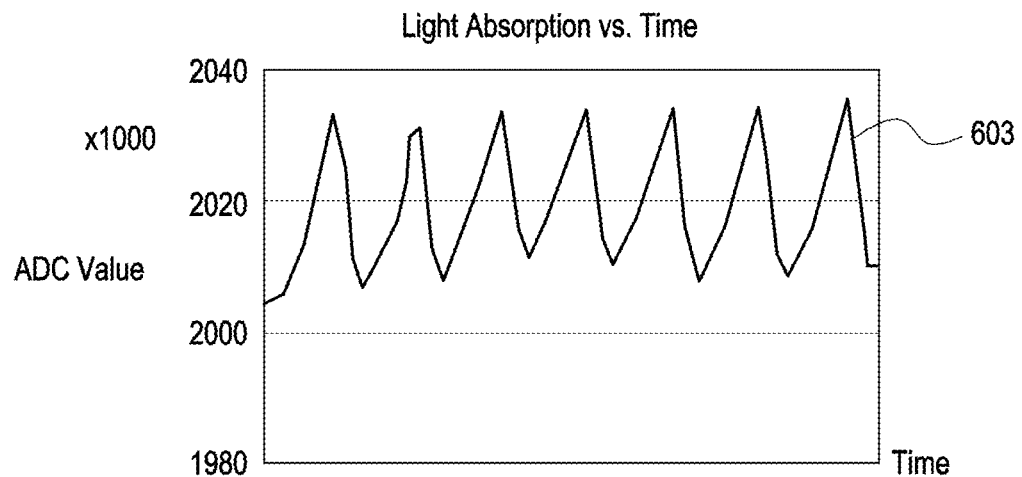
FIG. 6B illustrates a diagram of a PPG signal measured through a PPG sensor of an electronic device according to various embodiments.

FIG. 6A illustrates a diagram of a PPG signal measured through a PPG sensor (e.g., the biometric-information measurement sensor module 230 and/or the PPG sensor 301) of an electronic device (e.g., the electronic device 101, the electronic device 201, and/or the electronic device 401) according to various embodiments, and FIG. 6B illustrates a diagram of a PPG signal measured through a PPG sensor (e.g., the biometric-information measurement sensor module 230 and/or the PPG sensor 301) of an electronic device (e.g., the electronic device 101, the electronic device 201, and/or the electronic device 401) according to various embodiments.

If at least one LED of the PPG sensor emits light, some of the light may reach the blood vessels in the skin (e.g., arterial blood), and the light is absorbed in a manner that changes with a change in the blood flow rate, and the remaining light is reflected or scattered to thus reach at least one photodiode of the PPG sensor. The light reaching at least one photodiode of the PPG sensor may be output as PPG signal waveforms 601 and 603 as shown in FIGS. 6A and 6B.

For example, the light reaching at least one photodiode of the PPG sensor may be output as an AC component, which may be referred to as an "AC signal". The AC component of the PPG signal may exist together with a DC component (a DC signal) due to absorption and scattering of light in the skin, rather than the blood vessel or due to the light emitted from an external light source, rather than the light generated by the at least one LED of the PPG sensor.

For example, the AC signal may be a first parameter including information on the amount of light that is emitted from the LED, passes through the blood vessel of the user, and is reflected thereby to then be received by the light-receiving module (e.g., the light-receiving module 320).

For example, the DC signal may be a second parameter including information on the amount of light that is emitted from the LED, passes through a living tissue other than the blood vessel of the user, and is reflected thereby to then be received by the light-receiving module (e.g., the light-receiving module 320).

Figure 7:
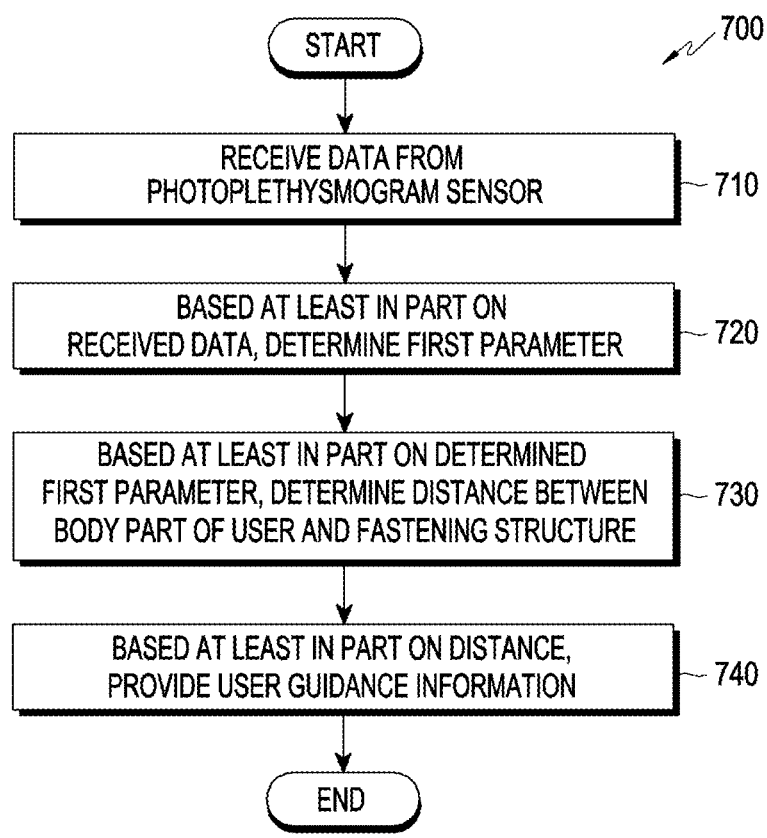
FIG. 7 illustrates a flowchart of a biometric information detection operation of an electronic device according to various embodiments.

FIG. 7 illustrates a flowchart 700 of a biometric information detection operation of an electronic device (e.g., the electronic device 101, the processor 120 of the electronic device 101, the electronic device 201, the processor 290 of the electronic device 201, and/or the electronic device 401) according to various embodiments.

In operation 710, the electronic device may receive data from a PPG sensor (e.g., the biometric-information measurement sensor module 230).

According to an embodiment, the electronic device may measure a biometric signal (e.g., blood pressure) from a body part of the user through the PPG sensor and may identify data according to the measurement of the biometric signal.

In operation 720, the electronic device may determine a first parameter, based at least in part on the received data.

According to an embodiment, the first parameter may include information on the amount of light (e.g., an AC signal of the PPG signal), which is emitted from at least one LED (e.g., the light-emitting module 310) included in the PPG sensor, passing through the blood vessel (e.g., an artery) of the user which is reflected thereby to then be received by the light-receiving module (e.g., the light-receiving module 320) of the PPG sensor.

In operation 730, the electronic device may determine the distance between a body part of the user and a fastening structure (e.g., the fastening structure 430) of the electronic device, based at least in part on the determined first parameter.

According to an embodiment, the electronic device may store information on the distances (e.g., distance values) between a body part of the user and the fastening structure of the electronic device, which corresponds to one or more first parameters, in a memory (e.g., the memory 130 and/or the memory 280). For example, the electronic device may identify the distance information (e.g., the distance value) between the body part of the user and the fastening structure of the electronic device, which is stored in the memory of the electronic device to correspond to the first parameter, thereby determining the distance.

In operation 740, the electronic device may provide user guidance information based at least in part on the determined distance.

According to an embodiment, the electronic device may provide the user guidance information using a touch screen display (e.g., the display device 160 or the touch screen display 260) and/or a speaker (e.g., the sound output device 155).

According to an embodiment, the user guidance information may include guidance information for guiding the user to adjust the wearing state of the electronic device to be tighter or looser than the current state.

For example, if the determined distance is greater than a reference distance stored in the memory of the electronic device, the user guidance information may include information that guides the user to adjust the wearing state to be tighter by a specified reference value (i.e., information that guides the user to perform adjustment to reduce the distance between the body part and the electronic device by a specified reference value).

For example, if the determined distance is less than a reference distance stored in the memory of the electronic device, the user guidance information may include information that guides the user to adjust the wearing state to be looser by a specified reference value (i.e., information that guides the user to perform adjustment to increase the distance between the body part and the electronic device by a specified reference value). For example, if the reference distance stored in the memory is 0, the determined distance may include a negative value less than the reference distance 0. For example, the reference distance 0 may correspond to the state in which the electronic device comes into close contact with the users skin while the users skin is not pressed at all, and a negative value of less than 0 may correspond to the state in which the electronic device comes into tight contact with the users skin so that the users skin is pressed.

In the embodiment in FIG. 7 described above, the electronic device has been described as determining the distance between a body part of the user and the fastening structure of the electronic device, based at least in part on the first parameter, but according to another embodiment, the electronic device may determine the distance, based at least in part on the ratio of the first parameter to the second parameter.

For example, the electronic device may store, in the memory, information on the distance between a body part of the user and the fastening structure of the electronic device, which corresponds to the ratios of one or more first parameters to the second parameters.

For example, the electronic device may further determine a second parameter, based at least in part on the data received in operation 710, and may determine the ratio of the first parameter to the second parameter according to operation 720. The electronic device may identify the distance information between a body part of the user and the fastening structure of the electronic device, which is stored in the memory of the electronic device so as to correspond to the ratio of the first parameter to the second parameter, thereby determining the distance.

In connection with the embodiment in FIG. 7 above, it has been described that the electronic device determines the distance between a body part of the user and the fastening structure of the electronic device, based at least in part on the first parameter in operation 730, and provides user guidance information, based at least in part on the determined distance in operation 740. However, according to another embodiment, the electronic device may determine the degree of contact between a body part of the user and the fastening structure of the electronic device, based at least in part on the first parameter, and may provide user guidance information based at least in part on the determined degree of contact.

For example, the electronic device may store, in the memory (e.g., the memory 130 and/or the memory 280), the degrees of contact between a body part of the user and the fastening structure of the electronic device, which correspond to one or more first parameters. For example, the electronic device may identify the degree of contact between a body part of the user and the fastening structure of the electronic device, which is stored in the memory of the electronic device, corresponding to the first parameter, thereby determining the degree of contact.

For example, if the determined degree of contact is lower (less) than a reference degree of contact stored in the memory of the electronic device, the guidance information provided by the electronic device may include information for guiding the user to adjust the wearing state of the electronic device to be tighter by a specified reference value (e.g., information for guiding the user to perform adjustment to increase the degree of contact between the body part and the electronic device by a specified reference value).

For example, if the determined degree of contact is higher (greater) than a reference degree of contact stored in the memory of the electronic device, the guidance information provided by the electronic device may include information for guiding the user to adjust the wearing state of the electronic device to be looser by a specified reference value.

According to another embodiment, based at least in part on the ratio of the first parameter to the second parameter, the electronic device may determine the degree of contact between a body part of the user and the fastening structure of the electronic device, and, based at least in part on the determined degree of contact, may provide user guidance information.

For example, the electronic device may store, in the memory, the degrees of contact between a body part of the user and the fastening structure of the electronic device, which correspond to the ratios of one or more first parameters to second parameters. For example, the electronic device may further determine a second parameter, based at least in part on the data received in operation 710, and may identify the ratio of the first parameter to the second parameter according to operation 720. For example, the electronic device may identify the degree of contact between a body part of the user and the fastening structure of the electronic device, which is stored in the memory of the electronic device, so as to correspond to the ratio of the first parameter to the second parameter, thereby determining the degree of contact.

According to various embodiments, a method for detecting biometric information in an electronic device (e.g., the electronic device 101, the processor 120 of the electronic device 101, the electronic device 201, the processor 290 of the electronic device 201, and/or the electronic device 401) may include: receiving data from a photoplethysmogram sensor of the electronic device; based at least in part on the received data, determining a first parameter; based at least in part on the determined first parameter, determining a distance between a body part of the user and the electronic device; and based at least in part on the distance, providing user guidance information on the display of the electronic device.

According to various embodiments, the determining of the distance between a body part of the user and the electronic device may include: based at least in part on the received data, determining a second parameter; and, based at least in part on the determined first parameter and the second parameter, determining the distance.

According to various embodiments, the determining the distance between a body part of the user and the electronic device may include, based at least in part on a ratio of the determined first parameter to second parameter, determining the distance.

According to various embodiments, the photoplethysmogram sensor may include a light-receiving module including at least one light-emitting diode (LED) and at least one photodiode, and the first parameter may include information on the amount of light that is emitted from the light-emitting diode, passes through a blood vessel of the user, and is reflected thereby to then be received by the light-receiving module, and the second parameter may include information on the amount of light that is emitted from the light-emitting diode, passes through a living tissue other than the blood vessel of the user, and is reflected thereby to then be received by the light-receiving module.

According to various embodiments, the method may further include, based at least in part on the determined first parameter, adjusting the distance between the body part and the electronic device using an actuator module of the electronic device.

According to various embodiments, the electronic device may be a wearable device.

According to various embodiments, the method may further include, if the distance is greater than a reference distance stored in the memory of the electronic device, performing adjustment to reduce the distance between the body part and the electronic device by a specified reference value using an actuator module of the electronic device.

According to various embodiments, the method may further include, if the distance is less than a reference distance stored in the memory, performing adjustment to increase the distance between the body part and the electronic device by a specified reference value using an actuator module of the electronic device.

Figure 8:
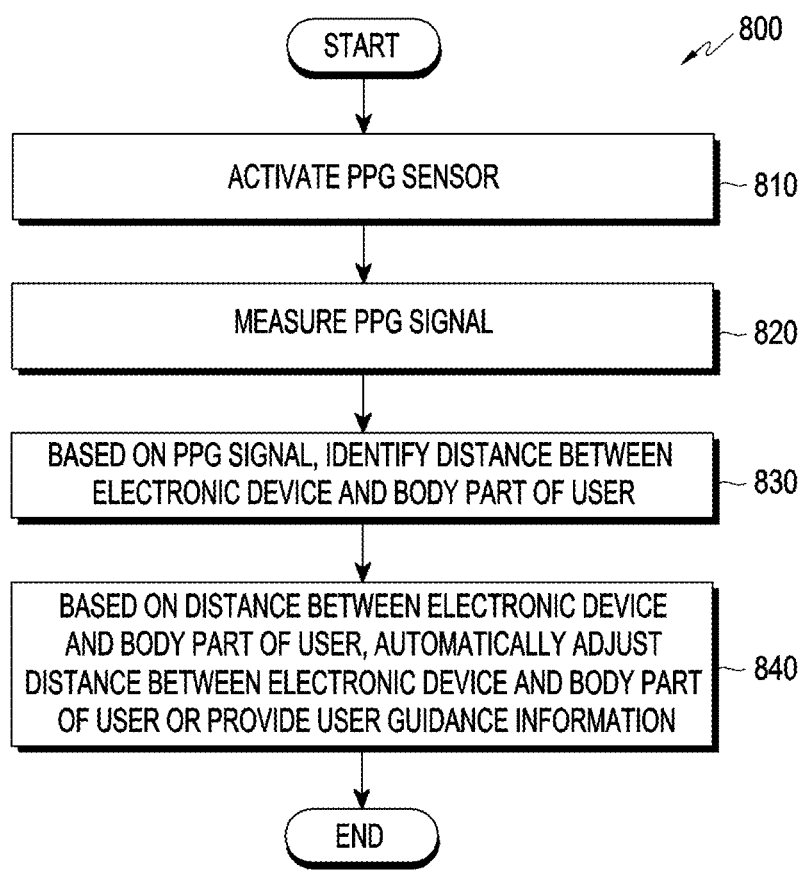
FIG. 8 illustrates a flowchart for controlling adjustment of a distance between an electronic device and a body part of a user according to various embodiments.

FIG. 8 illustrates a flowchart 800 for controlling adjustment of a distance between an electronic device (e.g., the electronic device 101, the processor 120 of the electronic device 101, the electronic device 201, the processor 290 of the electronic device 201, and/or the electronic device 401) and a body part of a user according to various embodiments.

In operation 810, the electronic device may activate a PPG sensor (e.g., the biometric-information measurement sensor module 230 and/or the PPG sensor 301).

According to an embodiment, the electronic device may be worn on a body part of the user, and may activate the PPG sensor to initiate measurement of users PPG signal s.

According to an embodiment, the electronic device may identify specified status information, and may automatically activate the PPG sensor, based on the status information.

For example, the electronic device may identify its own status information, based on at least one piece of schedule information stored in a memory (e.g., the memory 130 and/or the memory 280) of the electronic device, location information of the electronic device, which is obtained through a communication module of the electronic device (e.g., the communication module 190 and/or the wireless communication circuit 270), acceleration information of the electronic device, which is obtained through a sensor module (e.g., the sensor module 176) of the electronic device, or current time information.

For example, the status information may include information on the exercise status of the user, such as swimming or running.

For example, exercise schedule information may be stored in the memory of the electronic device, and if the current time corresponds to the time of the exercise schedule information, the electronic device may determine that the user is currently exercising and may activate the PPG sensor.

For example, the electronic device may identify location information of the electronic device using the communication module. For example, the electronic device may identify the location information by at least one of a cell positioning system (CPS) using a mobile communication base station, a global positioning system (GPS) utilizing satellites, or a Wi-Fi-based positioning system using a wireless access point. For example, the location information may include information indicating that the electronic device is currently located in a gym. For example, if it is confirmed that the electronic device is located in a gym, the electronic device may determine that the user is currently exercising, and may activate the PPG sensor.

For example, the location information may include information indicating that the electronic device is moving. For example, the electronic device may check the acceleration of the electronic device using an acceleration sensor, and may identify that the acceleration value of the electronic device continuously changes. For example, if the electronic device identifies that the location thereof changes for more than a specified period of time using the communication module (e.g., the global positioning system (GPS)) and/or that the acceleration value changes, the electronic device may determine that the user carrying or wearing the electronic device is exercising and may activate the PPG sensor.

According to another embodiment, the PPG sensor may be activated based on user input (user input to a biometric measurement icon and/or selection of a function for an exercise mode of the electronic device).

In operation 820, the electronic device may measure a PPG signal through the activated PPG sensor.

According to an embodiment, as a blood flow rate in the blood vessel under the users skin increases, the intensity of the PPG signal measured through the PPG sensor may increase because the amount of light absorption increases. The PPG signal may include an alternating current (AC) component and a direct current (DC) component.

According to an embodiment, the waveform of the measured PPG signal may be in the form of a PPG signal waveform 601 or 603 as shown in FIGS. 6A and 6B.

According to an embodiment, the electronic device may separate the PPG signal into an AC signal and a DC signal. For example, the electronic device may identify the magnitude of an AC signal value of the PPG signal and/or the magnitude of a DC signal value of the PPG signal. For example, the electronic device may identify the ratio of the magnitude of the AC signal value to the magnitude of the DC signal value (AC signal value/DC signal value) of the PPG signal.

In operation 830, the electronic device may determine the distance between the electronic device and a body part of the user, based on the measured PPG signal.

According to an embodiment, the distance between the electronic device and a body part of the user may include the degree of contact between the electronic device and a body part of the user.

According to an embodiment, based on the AC signal value of the PPG signal or based on the ratio of magnitude of the AC signal value to the magnitude of the DC signal value of the PPG signal, the electronic device may identify the distance between the electronic device and a body part of the user (the degree of contact between the electronic device and a body part of the user).

For example, the electronic device may store AC signal values of the PPG signals corresponding to respective ones of one or more distances between the electronic device and a body part of the user (the degrees of contact between the electronic device and a body part of the user) and may identify the distance between the electronic device and a body part of the user corresponding to the AC signal value of the measured PPG signal.

As another example, the electronic device may store ratios of magnitudes of the AC signal values to the magnitudes of the DC signal values of the PPG signals corresponding to respective ones of one or more distances between the electronic device and a body part of the user (the degrees of contact between the electronic device and a body part of the user), and may identify the distance between the electronic device and a body part of the user corresponding to the ratio of the magnitude of the AC signal value to the magnitude of the DC signal value of the PPG signal.

In operation 840, based on the identified distance between the electronic device and a body part of the user, the electronic device may automatically adjust the distance between the electronic device and the body part of the user or may provide user guidance information for guiding the wearing of the electronic device.

According to an embodiment, the electronic device may compare the reference distance stored when measuring a previous PPG signal using the PPG sensor with the identified distance between the electronic device and a body part of the user and may automatically perform adjustment to increase or reduce the distance between the electronic device and a body part of the user by a specified value (automatically adjust the degree of tightening of the electronic device with respect to a body).

According to an embodiment, if the electronic device includes a first fastener (e.g., the first fastener 450) and a second fastener (e.g., the second fastener 460), and in the case where the first fastener is coupled to the second fastener, the electronic device may perform control such that the first fastener moves in a first direction (e.g., the first direction 490) or in a second direction (e.g., the second direction 495) by a specified distance using a motor (e.g., the motor 441).

For example, if the identified distance between the electronic device and a body part of the user is greater than the stored reference distance, the electronic device may move the first fastener in the first direction by the specified distance. As the first fastener moves in the first direction, the distance between the electronic device and a body part of the user may be reduced. For example, the degree of tightening of the electronic device worn on a body part of the user with respect to the body part may be increased, so that the electronic device may move closer to the body part of the user by the specified distance.

For example, if the identified distance between the electronic device and a body part of the user is less than the stored reference distance, the electronic device may move the first fastener in the second direction by the specified distance. As the first fastener moves in the second direction, the distance between the electronic device and the body part of the user may be increased. For example, the degree of tightening of the electronic device worn on a body part of the user with respect to the body part may be reduced, so that the electronic device may be further spaced apart from the body part of the user by the specified distance.

According to an embodiment, the electronic device may compare the stored reference distance with the identified distance between the electronic device and the body part of the user and may provide user guidance information indicating that the distance between the electronic device and the body part of the user should be reduced or increased by a specified value.

For example, the electronic device may display the user guidance information of the electronic device on the touch screen display and/or may output the same as a sound via a speaker of the electronic device.

For example, the user guidance information of the electronic device may include information suggesting that the first fastener of the electronic device should be moved in the first direction by the specified distance if the identified distance between the electronic device and a body part of the user is greater than the stored reference distance.

For example, the user guidance information of the electronic device may include information suggesting that the first fastener of the electronic device should be moved in the second direction by the specified distance if the identified distance between the electronic device and a body part of the user is less than the stored reference distance.

Figure 9:
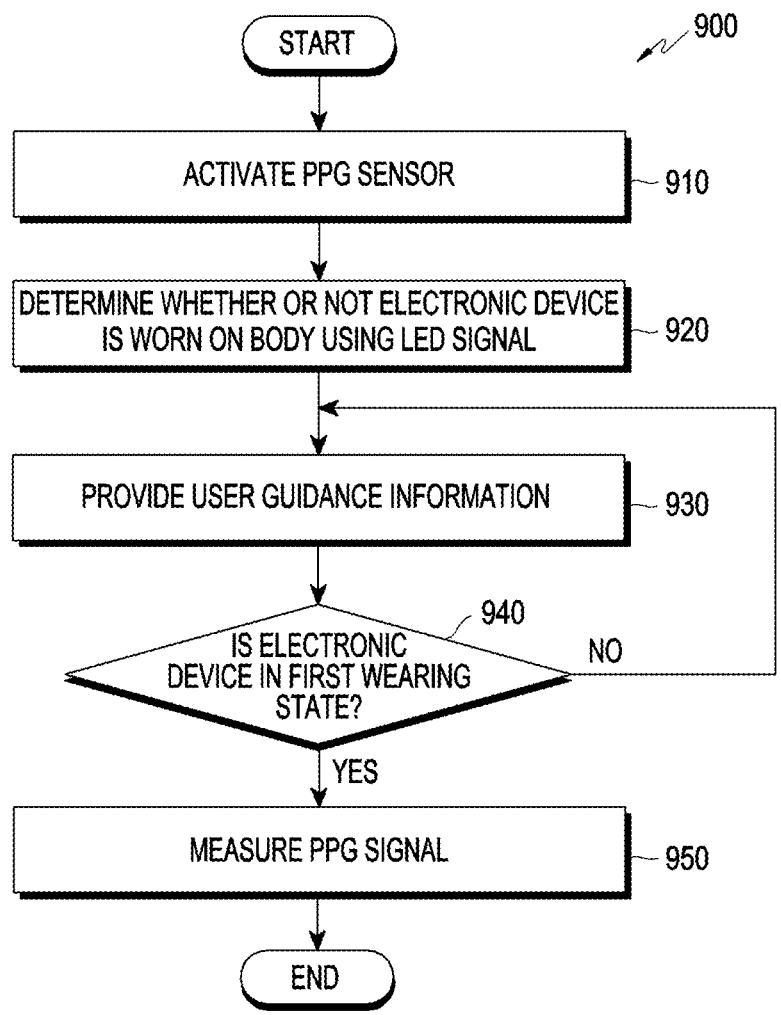
FIG. 9 illustrates a flowchart of a biometric information detection operation of an electronic device according to various embodiments.
Figures 10A, 10B, 10C, 10D:
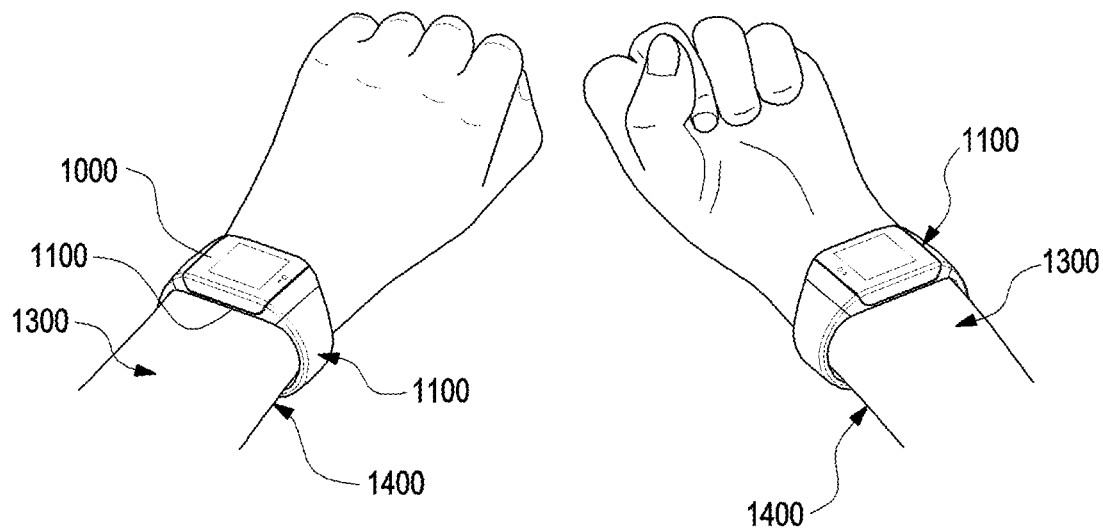
FIG. 10A illustrates a diagram for explaining a wearing state of an electronic device on a body part of a user according to various embodiments.
FIG. 10B illustrates a diagram for explaining a wearing state of an electronic device on a body part of a user according to various embodiments.
FIG. 10C illustrates a diagram for explaining a wearing state of an electronic device on a body part of a user according to various embodiments.
FIG. 10D illustrates a diagram for explaining a wearing state of an electronic device on a body part of a user according to various embodiments.

FIG. 9 illustrates a flowchart 900 of a biometric information detection operation of an electronic device (e.g., the electronic device 101, the processor 120 of the electronic device 101, the electronic device 201, the processor 290 of the electronic device 201, and/or the electronic device 401) according to various embodiments. FIG. 10A illustrates a diagram for explaining the wearing state of an electronic device (e.g., the electronic apparatus 101, the electronic apparatus 201, and/or the electronic apparatus 401) on a body part of a user according to various embodiments, FIG. 10B illustrates a diagram for explaining the wearing state of an electronic device (e.g., the electronic apparatus 101, the electronic apparatus 201, and/or the electronic apparatus 401) on a body part of a user according to various embodiments, FIG. 10C illustrates a diagram for explaining the wearing state of an electronic device (e.g., the electronic apparatus 101, the electronic apparatus 201, and/or the electronic apparatus 401) on a body part of a user according to various embodiments, and FIG. 10D illustrates a diagram for explaining the wearing state of an electronic device (e.g., the electronic apparatus 101, the electronic apparatus 201, and/or the electronic apparatus 401) on a body part of a user according to various embodiments.

Referring to FIG. 9, a PPG sensor (e.g., the biometric-information measurement sensor module 230 and/or the PPG sensor 301) may be activated in operation 910.

According to an embodiment, the electronic device may activate the PPG sensor in order to initiate measurement of users PPG signal s.

For example, the PPG sensor may include a light-emitting module and a light-receiving module. The light-emitting module may include an IR LED, a red LED, a green LED, and/or a blue LED. The light-receiving module may include one or more photodiodes.

For example, the electronic device may measure LED signals using at least one LED included in the PPG sensor.

In operation 920, the electronic device may determine whether or not the electronic device is worn on the body using the LED signal measured through the PPG sensor.

According to an embodiment, the electronic device may compare the measured LED signal value with a specified reference signal value to determine whether or not the electronic device is worn on the body. For example, if the identified LED signal value is greater than the reference signal value, the electronic device may determine that the electronic device is worn on a body part of the user. Otherwise, the electronic device may determine that the electronic device is not worn on a body part of the user. For example, the measured LED signal value may include an IR value of the IR LED.

In operation 930, the electronic device may provide user guidance information for guiding the wearing state of the electronic device.

According to an embodiment, the electronic device may provide the user with the user guidance information using a touch screen display and/or a speaker of the electronic device.

According to an embodiment, the user guidance information may include information about a first wearing state as shown in FIG. 10A. The first wearing state may refer to the state in which a first surface 1100 (e.g., the second portion 410b) of the electronic device 1000 is positioned on a first part 1300 (e.g., an upper part of the wrist) of the users body.

For example, the determination to provide, as the user guidance information, the information on the first wearing state as shown in FIG. 10A may be made by measuring the PPG signals in the case where the electronic device 1000 is in the first wearing state as shown in FIG. 10A and in the case where the electronic device 1000 is in a second wearing state in which the first surface 1100 of the electronic device 1000 is positioned on a second part 1400 (e.g., a lower part of the wrist) of the user's body as shown in FIG. 10B under the same experimental conditions. The measurement results of the PPG signals according to the first wearing state of the electronic device as shown in FIG. 10A and the second wearing state of the electronic device as shown in FIG. 10B will be described in detail later with reference to FIGS. 11A to 11D.

In operation 940, the electronic device may determine whether or not the electronic device is in the first wearing state (e.g., the first wearing state as shown in FIG. 10A).

According to an embodiment, the electronic device may determine whether or not the electronic device is in the first wearing state using an acceleration sensor included in the motion sensor module (e.g., the motion sensor module 240).

For example, the electronic device may compare a Z-axis acceleration value, measured using the acceleration sensor, with a specified reference Z-axis acceleration range (value), thereby determining the wearing state of the electronic device. For example, if the measured Z-axis acceleration value is included in the specified reference Z-axis acceleration range, the electronic device may determine that the electronic device is in the first wearing state in which the first surface of the electronic device is positioned on the first part of the user's body.

For example, in the first wearing state as shown in FIG. 10A, the electronic device 1000 may acquire acceleration values using the acceleration sensor as shown in FIG. 10C in which the X-axis acceleration value is 32624, the Y-axis acceleration value is 31507, and the Z-axis acceleration value is 36653.

For example, in the second wearing state as shown in FIG. 10B, the electronic device 1000 may acquire acceleration values using the acceleration sensor as shown in FIG. 10D, in which the X-axis acceleration value is 32056, the Y-axis acceleration value is 30122, and the Z-axis acceleration value is 29693.

For example, comparing the acceleration values in FIG. 10C with the acceleration values in FIG. 10D, it can be seen that the difference between the Z-axis acceleration values is quite large, compared to the difference between the X-axis acceleration values or the difference between the Y-axis acceleration values, depending on the wearing state of the electronic device. Based on this result, the Z-axis acceleration values of the acceleration sensor may be used in determining the wearing state of the electronic device as described above. For example, the specified reference Z-axis acceleration range (value) may be determined by means of an experiment of measuring the Z-axis acceleration value through the acceleration sensor in the first wearing state of the electronic device 1000 as shown in FIG. 10A and/or measuring the Z-axis acceleration value through the acceleration sensor in the second wearing state of the electronic device 1000 as shown in FIG. 10B. For example, the electronic device 1000 may determine the specified Z-axis acceleration value (range), based on the maximum value, the minimum value, and/or the average value of the Z-axis acceleration values measured through the above experiment.

According to an embodiment, the electronic device may execute operation 950 if it is determined that the electronic device is in the first wearing state. Otherwise, the electronic device may execute operation 930 again.

In operation 950, the electronic device may measure a PPG signal.

According to an embodiment, the electronic device may measure the PPG signal of the user using the PPG sensor.

Figure 11A:
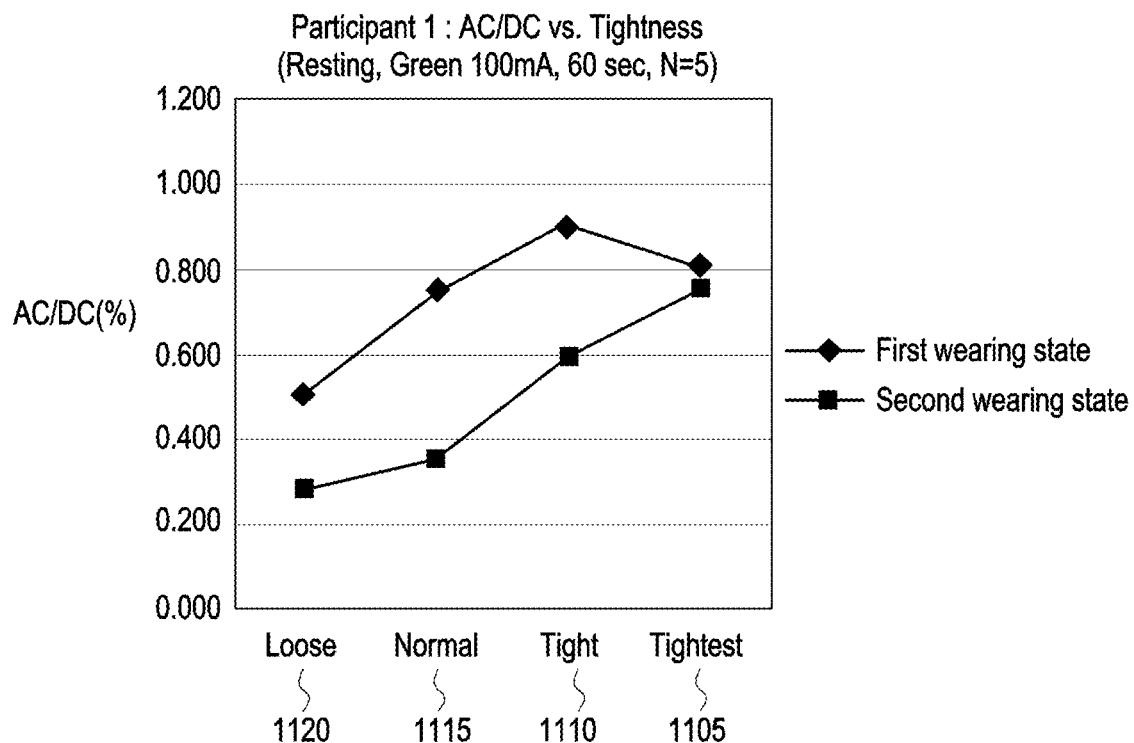
FIG. 11A illustrates a diagram for explaining a difference in the PPG signal of a user obtained according to the wearing state of the electronic device according to various embodiments.
Figure 11B:
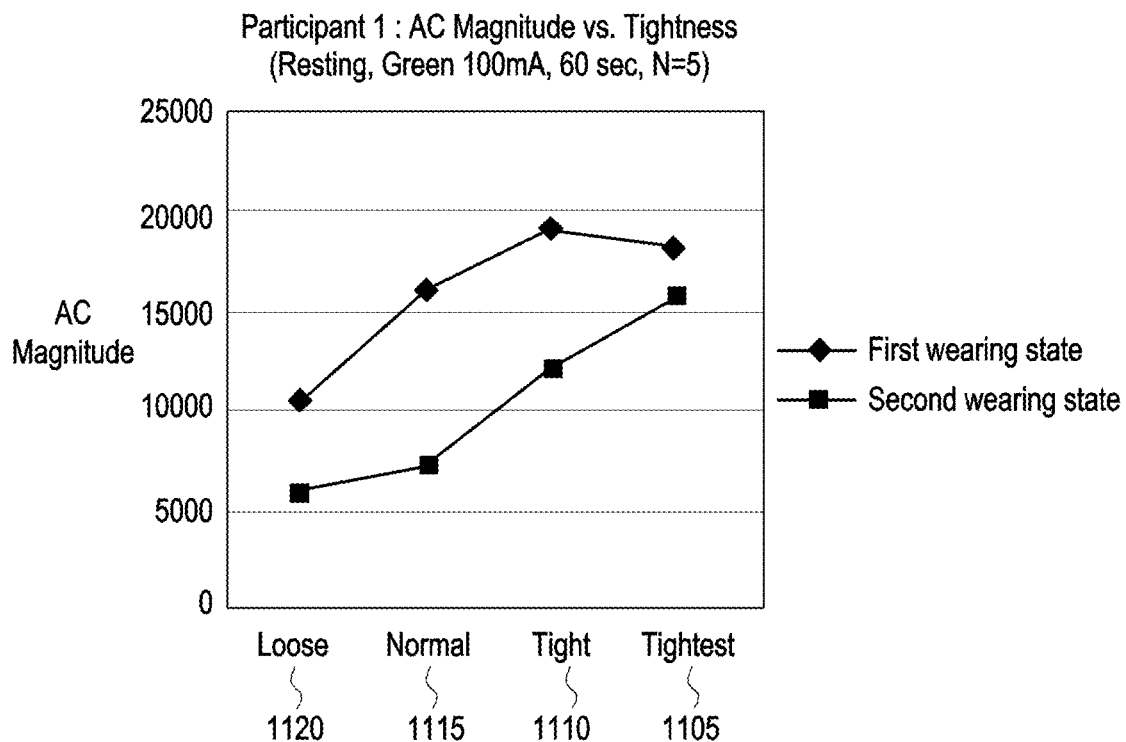
FIG. 11B illustrates a diagram for explaining a difference in a PPG signal of a user obtained according to the wearing state of the electronic device according to various embodiments.
Figure 11C:
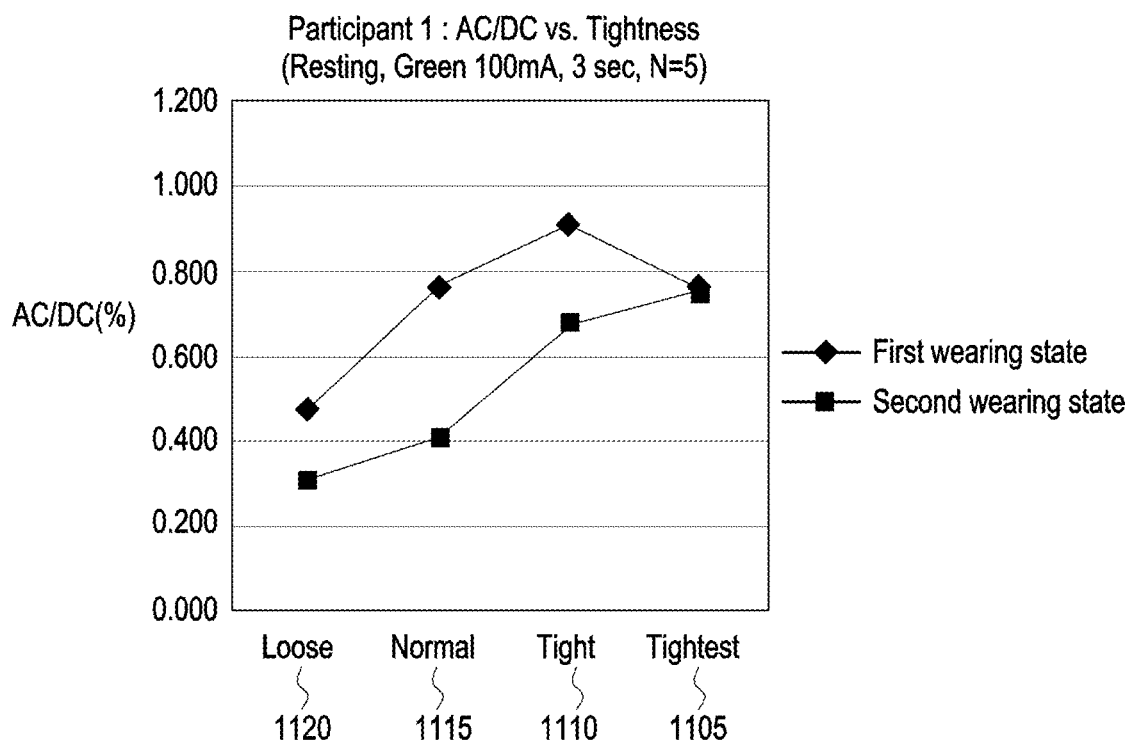
FIG. 11C illustrates a diagram for explaining a difference in a PPG signal of a user obtained according to the wearing state of the electronic device according to various embodiments.
Figure 11D:
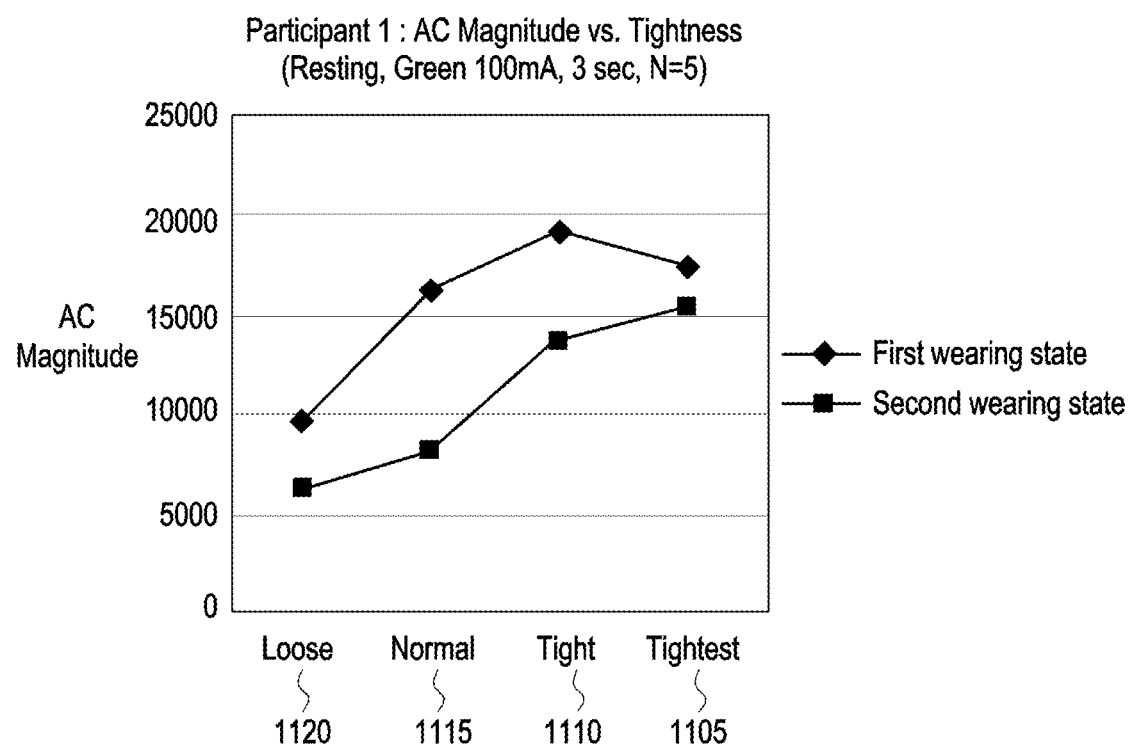
FIG. 11D illustrates a diagram for explaining a difference in a PPG signal of a user obtained according to the wearing state of the electronic device according to various embodiments.

FIG. 11A illustrates a diagram for explaining the difference in the PPG signal of a user obtained according to the wearing state of the electronic device according to various embodiments. FIG. 11B illustrates a diagram for explaining the difference in the PPG signal of a user obtained according to the wearing state of the electronic device according to various embodiments. FIG. 11C illustrates a diagram for explaining the difference in the PPG signal of a user obtained according to the wearing state of the electronic device according to various embodiments. FIG. 11D illustrates a diagram for explaining the difference in the PPG signal of a user obtained according to the wearing state of the electronic device according to various embodiments.

According to an embodiment, the electronic device (e.g., the electronic device 101, the electronic device 201, the electronic device 401, and/or the electronic device 1000) measures PPG signals under specified experimental conditions, and may produce a graph of variation of the ratio of an AC signal value to a DC signal value of the PPG signal obtained by the electronic device according to the wearing state of the electronic device, as shown in FIG. 11A, and a graph of variation of the AC amplitude of the PPG signal obtained by the electronic device according to the wearing state, as shown in FIG. 11B.

An experiment was conducted such that the electronic device measured PPG signals of a specific user five times at different times using the green LED of the PPG sensor. In addition, PPG signals in four contact states between the electronic device and the users skin we re measured in each measurement, and the PPG signals were measured for 60 seconds for each contact state.

The four contact states between the electronic device and the users skin are defined as a first contact state (a tightest state) 1105 in which the straps of the electronic device can be tightened no further, so that the user feels a discomfort on the wrist while wearing the electronic device, a second contact state (a tight state) 1110, in which the straps of the electronic device are loosened by a first length from the first contact state, a third contact state (a normal state) 1115 in which the straps of the electronic device are loosened by a second length from the first contact state, and a fourth contact state (a loose state) 1120 in which the straps of the electronic device are loosened by a third length from the first contact state.

For example, according to the above experimental conditions, the electronic device calculated the ratios of AC signal values/DC signal values of the PPG signals, which are measured in the first to fourth contact states 1105, 1110, 1115, and 1120, and the average of the amplitudes of the AC signals of the PPG signals for each time.

Referring to FIG. 11A, as a result of measuring the PPG signals of the user in the first wearing state as shown in FIG. 10A according to the above experimental conditions, the ratios of the AC signal values/DC signal values were 0.8% in the first contact state 1105, 0.9% in the second contact state 1110, 0.75% in the third contact state 1115, and 0.5% in the fourth contact state 1120, respectively. As a result of measuring the PPG signals of the user in the second wearing state as shown in FIG. 10B according to the above experimental conditions, the ratios of the AC signal values/DC signal values were 0.68% in the first contact state 1105, 0.6% in the second contact state 1110, 0.35% in the third contact state 1115, and 0.3% in the fourth contact state 1120, respectively.

Referring to FIG. 11B, as a result of measuring the PPG signals of the user in the first wearing state as shown in FIG. 10A according to the above experimental conditions, the magnitudes of the AC signals were 17000 in the first contact state 1105, 18000 in the second contact state 1110, 16000 in the third contact state 1115, and 11000 in the fourth contact state 1120, respectively. As a result of measuring the PPG signals of the user in the second wearing state as shown in FIG. 10B according to the above experimental conditions, the magnitudes of the AC signals were 16000 in the first contact state 1105, 13000 in the second contact state 1110, 7000 in the third contact state 1115, and 6000 in the fourth contact state 1120, respectively.

Referring to FIGS. 11A and 11B, it can be seen that as the wearing state of the electronic device on the users wrist becomes tight (i.e., as the distance between the electronic device and the skin is reduced) when the electronic device measures the PPG signals under the above experimental conditions, the ratio of an AC signal value to a DC signal value and the magnitude of an AC signal increase. In addition, the ratio of an AC signal value to a DC signal value and the magnitude of an AC signal in the first wearing state is greater than the ratio of an AC signal value to a DC signal value and the magnitude value of an AC signal in the second wearing state, and, based on the ratios of AC signal values to DC signal values and the magnitudes (maximum points) of AC signals in the second wearing state, the ratio of an AC signal value to a DC signal value and the AC signal value tend to be further reduced if the electronic device is worn on a body part of the user in the third contact state 1115 or the first contact state 1105.

In addition, it can be confirmed that the ratios of AC signal values to DC signal values and the magnitudes of AC signals in the first contact state 1105 are similar to each other between the first wearing state shown in FIG. 10A and the second wearing state shown in FIG. 10B. This is due to the fact that there is little difference in the gap between the electronic device and the users skin because the electronic device and the users skin come into very close contact with each other. For example, although the difference between the first wearing state and the second wearing state (i.e., the difference in the gap between the electronic device and the skin surface of the user) may be considered to be negligible to the naked eye in the second to fourth contact states 1110, 1115, and 1120, this difference may significantly affect the ratio of an AC signal value to a DC signal value and the magnitude of an AC signal to thus have a great effect on the accuracy of the PPG signal measurement. Although variation in the physical condition of the user whose PPG signals are to be measured may bring about a change in the ratio of an AC signal value to a DC signal value and the magnitude of an AC signal of the PPG signals in the same condition when measuring the PPG signals, it can be seen that the graphs thereof tend to be substantially similar to those in FIGS. 11A and 11B.

According to an embodiment, the same raw data as the experimental conditions may be used in consideration of a practical aspect of providing user guidance information for suggesting change of the wearing state of the electronic device or automatically adjusting the straps of the electronic device. For example, graphs of an average value for 3 seconds, instead of the graphs of an average value for 60 seconds as shown in FIGS. 11A and 11B, may be shown as illustrated in FIGS. 11C and 11D.

Referring to FIG. 11C, a graph of an average value for 3 seconds, other than the graphs of an average value for 60 seconds shown in FIGS. 11A and 11B, may be identified using the same raw data as in the above experimental conditions. For example, in the case of the PPG signals measured according to the above-described conditions in the first wearing state as shown in FIG. 10A, the ratio of an AC signal value to a DC signal value may be 0.75% in the first contact state 1105, 0.9% in the second contact state 1110, 0.75% in the third contact state 1115, and 0.45% in the fourth contact state 1120. Referring to FIG. 11D, if a graph of an average value for 3 seconds, instead of the graphs of an average value for 60 seconds as shown in FIGS. 11A and 11B, is identified using the same raw data as the above experimental conditions, the ratio of an AC signal value to a DC signal value of the PPG signals measured according to the above-described conditions in the second wearing state as shown in FIG. 10B may be 0.75% in the first contact state 1105, 0.68% in the second contact state 1110, 0.4% in the third contact state 1115, and 0.3% in the fourth contact state 1120.

Referring to FIG. 11D, if a graph of an average value for 3 seconds, instead of the graphs of an average value for 60 seconds as shown in FIGS. 11A and 11B, is identified using the same raw data as the above experimental conditions, the magnitude of an AC signal of the PPG signals measured according to the above-described conditions in the first wearing state as shown in FIG. 10A may be 17000 in the first contact state 1105, 18500 in the second contact state 1110, 16000 in the third contact state 1115, and 10000 in the fourth contact state 1120. Referring to FIG. 11D, if a graph of an average value for 3 seconds, instead of the graphs of an average value for 60 seconds as shown in FIGS. 11A and 11B, is identified using the same raw data as the above experimental conditions, the magnitude of an AC signal of the PPG signals measured according to the above-described conditions in the second wearing state as shown in FIG. 10B may be 15500 in the first contact state 1105, 14000 in the second contact state 1110, 8000 in the third contact state 1115, and 7000 in the fourth contact state 1120.

Referring to FIGS. 11C and 11D, although the average values of the ratios of AC signal values to DC signal values and the magnitudes of AC signals for 3 seconds are slightly different from those for 60 seconds in FIGS. 11A and 11B, it can be seen that the tendency of the graph is maintained. For example, if the electronic device measures the pulse period only once, the time used in calculating the average value may be reduced to about 1.5 seconds, but this may not ensure the reliability of the calculated value of the PPG signal. For example, in order to improve the reliability of the calculated value of the PPG signal, the electronic device may calculate an average value of the ratios of AC signal values to DC signal values and the magnitudes of AC signals for 3 seconds including at least two pulse periods.

Although not shown, according to an embodiment, an experiment for identifying the value of AC signal value/DC signal value and the magnitude of an AC signal according to a change in the wearing state of the electronic device with respect to another participant having different physical conditions was performed in order to compare the result thereof with the results shown in FIGS. 11A to 11D. Although the standard deviation was slightly increased, compared to the participant of the results shown in FIGS. 11A to 11D, the result in which both the ratio of an AC signal value to a DC signal value and the magnitude of an AC signal in the first wearing state as shown in FIG. 10A are maximized in the second contact state 1110 was repeated, and the tendency in which the measurement values become similar to each other between the first wearing state shown in FIG. 10A and the second wearing state shown in FIG. 10B in the first contact state 1105 was confirmed. For example, using a combination of the ratios of AC signal values/DC signal values or the magnitudes of AC signals of four wavelengths obtained by using the IR LED, the red LED, and the blue LED, as well as the green LED, in a manner similar to the above experimental conditions, the electronic device may further optimize the wearing state of the electronic device on the user for measurement of the PPG signals, thereby further improving the reliability of the users biometric information.

Figure 12A:
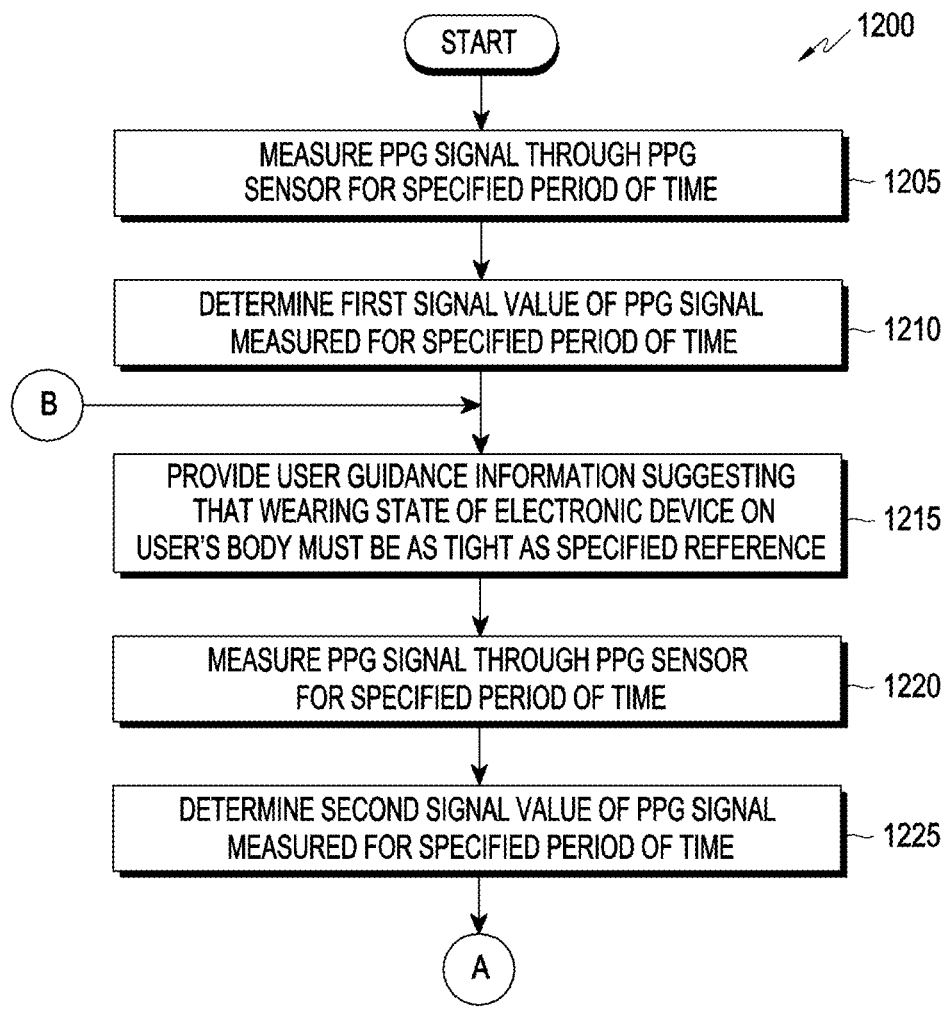
FIG. 12A illustrates a flowchart of a biometric information detection operation of an electronic device according to various embodiments.
Figure 12B:
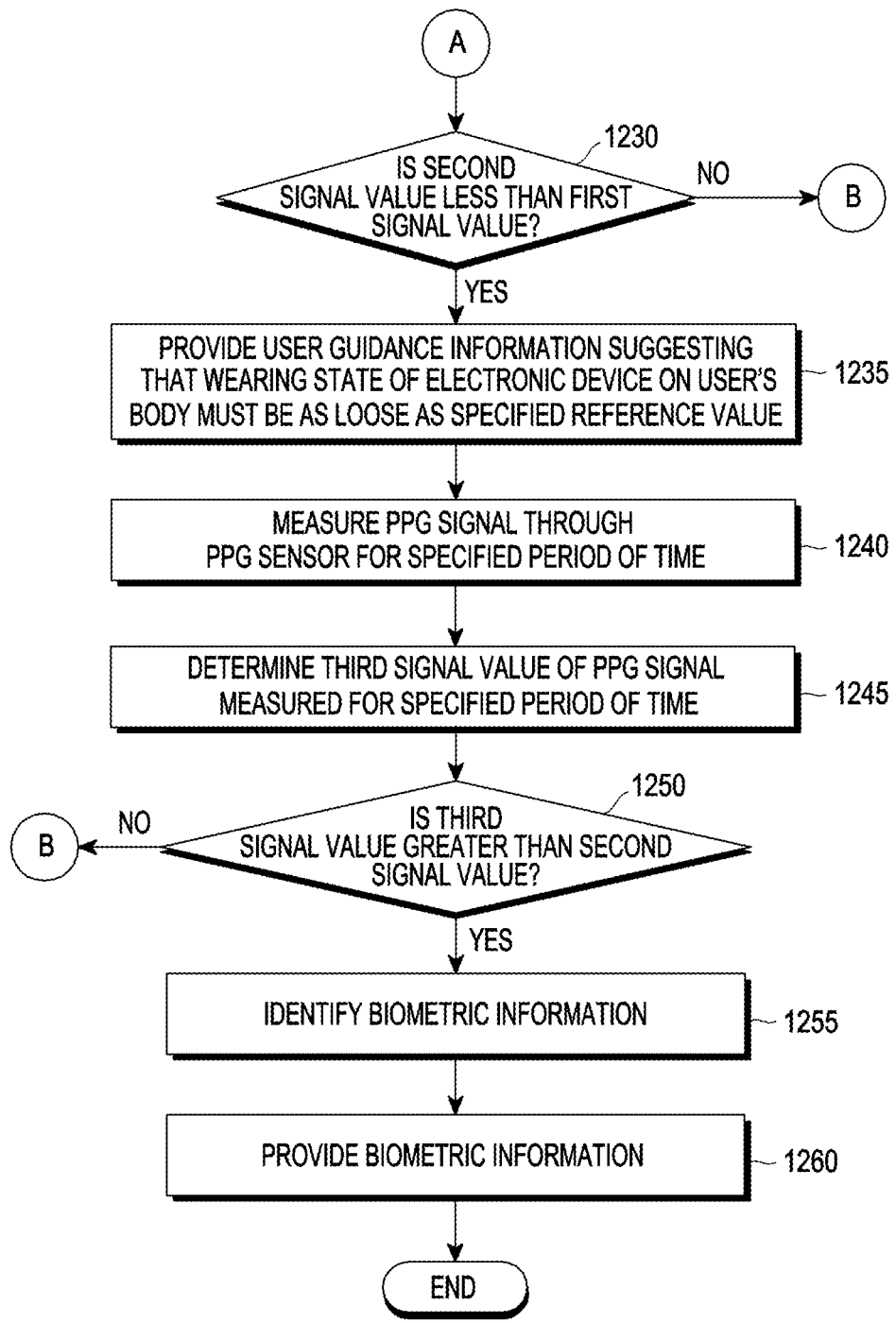
FIG. 12B illustrates a flowchart of a biometric information detection operation of an electronic device according to various embodiments.

FIG. 12A illustrates a flowchart 1200 of a biometric information detection operation of an electronic device (e.g., the electronic device 101, the processor 120 of the electronic device 101, the electronic device 201, the processor 290 of the electronic device 201, and/or the electronic device 401) according to various embodiments, and FIG. 12B illustrates a flowchart 1200 of a biometric information detection operation of an electronic device (e.g., the electronic device 101, the processor 120 of the electronic device 101, the electronic device 201, the processor 290 of the electronic device 201, and/or the electronic device 401) according to various embodiments.

Referring to FIGS. 12A and 12B, the electronic device may measure an initial PPG signal of the user and may obtain the ratio of an AC signal value to a DC signal value (and/or the magnitude of an AC signal) of the initially measured PPG signal.

For example, the electronic device may measure the PPG signal for a specified period of time and may obtain the ratio of an AC signal value to a DC signal value (and/or the amplitude of an AC signal) of the PPG signal measured for the specified period of time.

For example, based on the obtained ratio of an AC signal value to a DC signal value (and/or the magnitude of an AC signal), the electronic device may provide user guidance information to guide the user to adjust the wearing state of the electronic device to be tighter or looser than the current wearing state. If the wearing state of the electronic device is adjusted by the user according to the user guidance information, the electronic device may measure the PPG signal again.

For example, the electronic device may obtain the ratio of an AC signal value to a DC signal value (and/or the magnitude of an AC signal) of the re-measured PPG signal, and may compare the same with the previously obtained values (stored values). According to the above comparison, the electronic device may determine whether the electronic device should be tightened or loosened and may provide the user with user guidance information of the electronic device according to the determination.

For example, the user may adjust the wearing state of the electronic device to be tighter or looser with reference to the user guidance information, thereby maintaining the optimal contact state between the electronic device and the users skin in order to obtain optimal biometric information of the user.

In operation 1205, the electronic device may measure a PPG signal through the PPG sensor for a specified period of time.

According to an embodiment, the specified period of time may be determined in consideration of the pulse period of the user. For example, the specified period of time may be 3 seconds or 60 seconds.

In operation 1210, the electronic device may determine a first signal value of the PPG signal measured for the specified period of time.

According to an embodiment, the first signal value may include a first parameter or a ratio of a first parameter to a second parameter. For example, the first parameter may include an AC signal value of the PPG signal, and the second parameter may include a DC signal value of the PPG signal.

In operation 1215, the electronic device may provide user guidance information suggesting that the wearing state of the electronic device on the user's body should be as tight as a specified reference.

According to an embodiment, the electronic device may provide the user guidance information via a display and/or a speaker.

According to an embodiment, if the electronic device is a wearable device worn on the users wrist, which has straps in which a plurality of holes are arranged at a predetermined interval, the specified reference may be one pitch between respective ones among the plurality of holes. For example, the electronic device may provide user guidance information to guide the user to adjust the current wearing state by reducing one pitch of the holes on the straps.

In operation 1220, the electronic device may measure a PPG signal through the PPG sensor for a specified period of time.

According to an embodiment, the electronic device may execute operation 1220 after a predetermined period of time has elapsed since the execution of operation 1215. For example, according to operation 1215 of the electronic device, the user may adjust the wearing state of the electronic device on the users body to be tighter than the current state, and the predetermined period of time may be determined in consideration of the time during which the user adjusts the wearing state.

According to an embodiment, the electronic device may execute operation 1220 upon identifying the change in the wearing state of the electronic device after performing operation 1215. For example, the electronic device may identify the change in the wearing state of the electronic device using the sensor module. For example, the electronic device may identify the change in the wearing state of the electronic device using a rotary encoder (e.g., the rotary encoder 443) included in an actuator module (e.g., the actuator module 440). For example, the electronic device may identify the change in the wearing state of the electronic device based on the measurement of the rotational angle of the rotary encoder.

In operation 1225, the electronic device may determine a second signal value of the PPG signal measured during the specified period of time.

According to an embodiment, the second signal value may include a first parameter or a ratio of a first parameter to a second parameter. For example, the first parameter may include an AC signal value of the PPG signal, and the second parameter may include a DC signal value of the PPG signal.

In operation 1230, the electronic device may identify whether or not the second signal value is less than the first signal value.

According to an embodiment, if the second signal value is less than the first signal value in operation 1230, the electronic device may perform operation 1235. Otherwise, the electronic device may perform operation 1215.

In operation 1235, the electronic device may provide user guidance information suggesting that the wearing state of the electronic device on the user's body should be as loose as a specified reference value.

According to an embodiment, the electronic device may provide wearing guidance information of the electronic device using a display and/or a speaker.

According to an embodiment, if the electronic device is a wearable device worn on the users wrist, which has straps in which a plurality of holes are arranged, the specified reference may be one pitch between respective ones among the plurality of holes. For example, the electronic device may provide user guidance information to guide the user to adjust the current wearing state by increasing one pitch of the holes on the straps.

In operation 1240, the electronic device may measure a PPG signal through the PPG sensor for a specified period of time.

According to an embodiment, the electronic device may execute operation 1240 after a predetermined period of time has elapsed since the execution of operation 1235. For example, according to operation 1235 of the electronic device, the user may adjust the wearing state of the electronic device on the users body to b e looser than the current state, and the predetermined period of time may be determined in consideration of the time during which the user adjusts the wearing state.

According to an embodiment, the electronic device may execute operation 1240 upon identifying the change in the wearing state of the electronic device after performing operation 1235. For example, the electronic device may identify the change in the wearing state of the electronic device using the sensor module. For example, the electronic device may identify the change in the wearing state of the electronic device using a rotary encoder (e.g., the rotary encoder 443) included in an actuator module (e.g., the actuator module 440). For example, the electronic device may identify the change in the wearing state of the electronic device, based on the measurement of the rotational angle of the rotary encoder.

In operation 1245, the electronic device may determine a third signal value of the PPG signal measured for the specified period of time.

According to an embodiment, the third signal value may include a first parameter or a ratio of a first parameter to a second parameter. For example, the first parameter may include an AC signal value of the PPG signal, and the second parameter may include a DC signal value of the PPG signal.

In operation 1250, the electronic device may determine whether or not the third signal value is greater than the second signal value.

According to an embodiment, if the third signal value is greater than the second signal value in operation 1250, the electronic device may perform operation 1255. Otherwise, the electronic device may perform operation 1215.

In operation 1255, the electronic device may identify biometric information.

According to an embodiment, based on the third signal value, the electronic device may identify the biometric information of the electronic device.

According to an embodiment, the electronic device may store the identified biometric information in the memory thereof.

In operation 1260, the electronic device may provide the identified biometric information.

According to an embodiment, the electronic device may provide the identified biometric information via a touch screen display and/or a speaker.

According to an embodiment, while the electronic device performs operations 1205 to 1260 in the embodiments shown in FIGS. 12A and 12B above, if one of the operations takes time exceeding the specified period of time, the electronic device may provide an error message to the user via the touch screen display and/or the speaker and may terminate the operations.

According to FIGS. 12A and 12B described above, the electronic device may obtain the signal value of the PPG sensor, which was initially measured, for a specified period of time, may then provide user guidance information to guide the user to adjust the straps of the electronic device to be tighter with respect to the users skin, may measure a signal value of the PPG signal again for a specified period of time, and may compare the same with a previously measured value. If the subsequently measured signal value is greater than the previously measured signal value as a result of the comparison, the terminal may provide user guidance information to further tighten the straps, and if the subsequently measured signal value is less than the previously measured signal value, the terminal may provide user guidance information to further loosen the straps. The electronic device may repeat the operation of providing user guidance information to tighten or loosen the straps, thereby guiding the user to manually adjust the wearing state of the electronic device, so that the electronic device may be brought into an optimal contact with the users skin. The electronic device may store, in the memory, the optimal distance between the electronic device and a body part of the user (i.e., the degree of contact between the electronic device and the users skin) after completing the measurement of the biometric information. When performing the above-described operation, if it takes more time than necessary to reach the optimized skin contact state, the electronic device may display an error message on the screen.

Figure 13A:
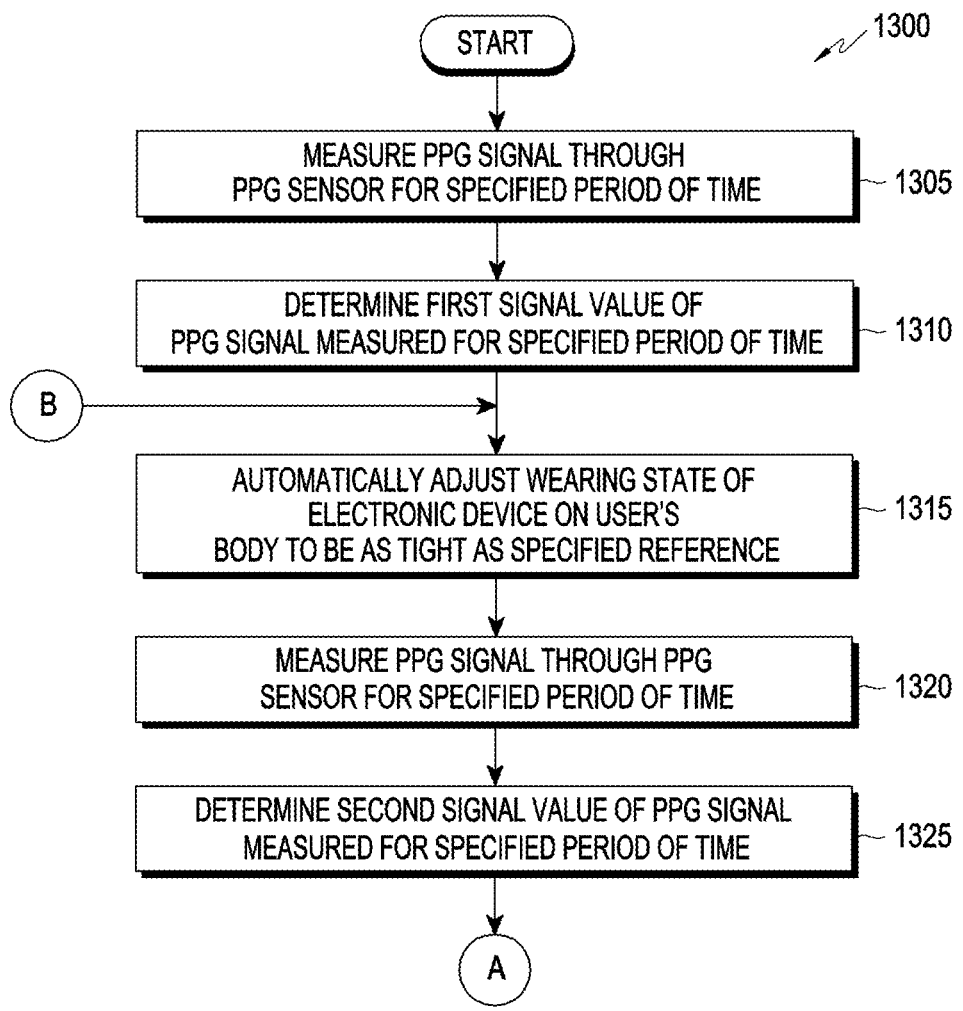
FIG. 13A illustrates a flowchart of a biometric information detection operation of an electronic device according to various embodiments.
Figure 13B:
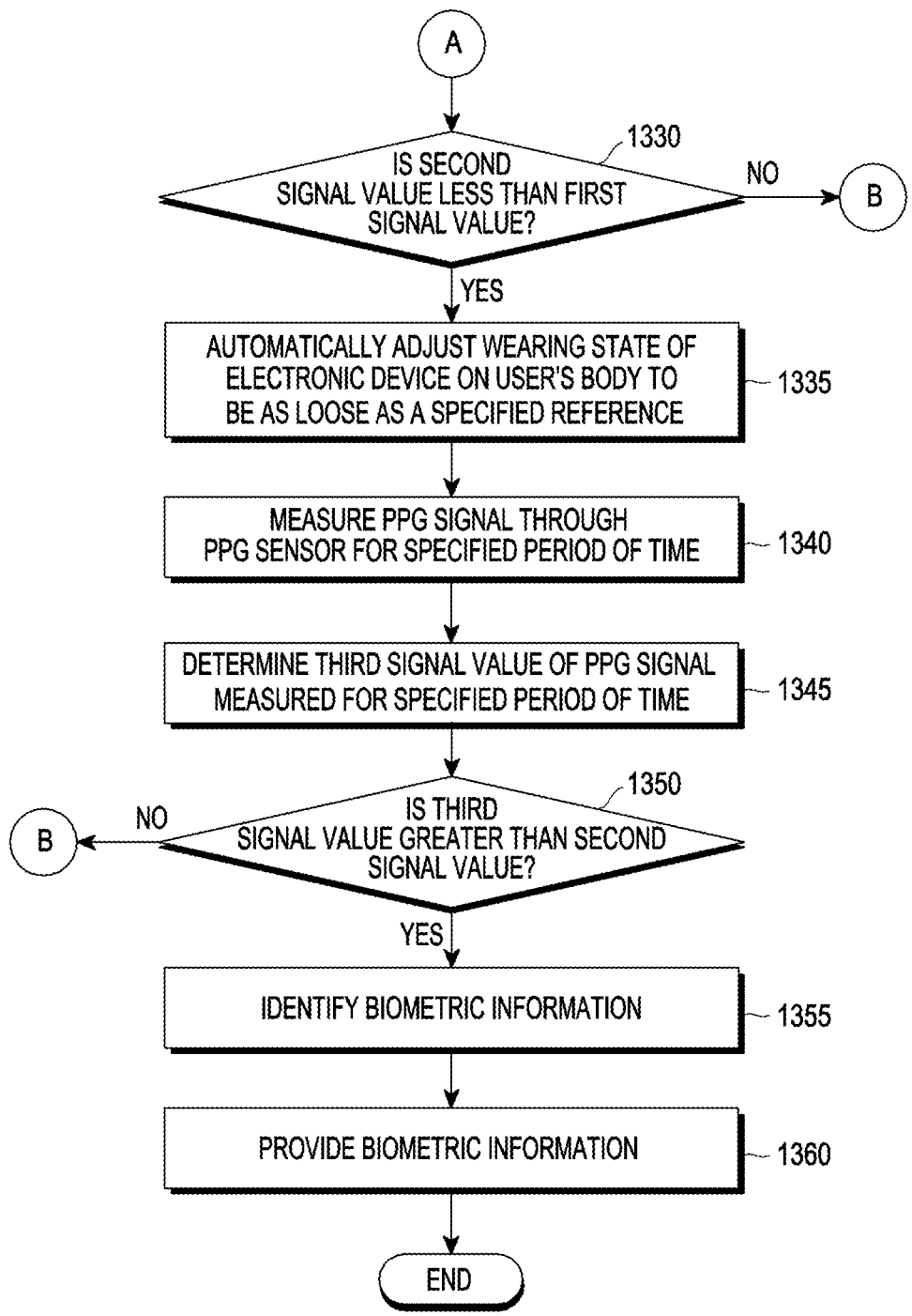
FIG. 13B illustrates a flowchart of a biometric information detection operation of an electronic device according to various embodiments.

FIG. 13A illustrates a flowchart 1300 of a biometric information detection operation of an electronic device (e.g., the electronic device 101, the processor 120 of the electronic device 101, the electronic device 201, the processor 290 of the electronic device 201, and/or the electronic device 401) according to various embodiments, and FIG. 13B illustrates a flowchart 1300 of a biometric information detection operation of an electronic device (e.g., the electronic device 101, the processor 120 of electronic device 101, the electronic device 201, the processor 290 of the electronic device 201, and/or the electronic device 401) according to various embodiments.

Referring to FIGS. 13A and 13B, the electronic device may measure an initial PPG signal of the user, and may obtain the ratio of an AC signal value to a DC signal value (and/or the magnitude of an AC signal) of the initially measured PPG signal.

For example, the electronic device may measure the PPG signal for a specified period of time and may obtain the ratio of an AC signal value to a DC signal value (and/or the amplitude of an AC signal) of the PPG signal. For example, based on the obtained ratio of an AC signal value to a DC signal value (and/or the magnitude of an AC signal), the electronic device may automatically adjust the wearing state of the electronic device to be tighter or looser than the current state.

For example, if the wearing state of the electronic device is automatically adjusted, the electronic device may again perform the measurement of the PPG signal. For example, the electronic device may obtain the ratio of an AC signal value to a DC signal value (and/or the magnitude of an AC signal) of the re-measured PPG signal, and may compare the same with the previously obtained values (stored values). According to the above comparison, the electronic device may adjust the wearing state of the electronic device to be tighter or looser, thereby providing an optimized contact state of the electronic device with respect to the users skin in order to obtain optimal biometric information of the user.

In operation 1305, the electronic device may measure a PPG signal through the PPG sensor for a specified period of time.

According to an embodiment, the specified period of time may be determined in consideration of the pulse period of the user. For example, the specified period of time may be 3 seconds or 60 seconds.

In operation 1310, the electronic device may determine a first signal value of the PPG signal measured for the specified period of time.

According to an embodiment, the first signal value may include a first parameter or a ratio of a first parameter to a second parameter. For example, the first parameter may include an AC signal value of the PPG signal, and the second parameter may include a DC signal value of the PPG signal.

In operation 1315, the electronic device may automatically adjust the wearing state of the electronic device on the user's body as tight as a specified reference.

According to an embodiment, the electronic device may include a first fastener (e.g., the first fastener 450) and a second fastener (e.g., the second fastener 460), and the first fastener may be moved in a first direction (e.g., the first direction 490) by a motor (e.g., the motor 441) of the electronic device while being coupled to the second fastener.

For example, the electronic device may move the first fastener in the first direction by a specified distance. According to the movement of the first fastener in the first direction, the degree of tightening of the electronic device worn on a body part of the user with respect to the body part of the user is further increased, thereby reducing the distance between the electronic device and the body part of the user corresponding to the specific distance.

According to an embodiment, the electronic device may provide information indicating that the wearing state of the electronic device is to be automatically adjusted before operation 1315 and/or may provide information indicating that the wearing state of the electronic device is being automatically adjusted at the same time as operation 1315 through a display and/or a speaker.

In operation 1320, the electronic device may measure a PPG signal through the PPG sensor for a specified period of time.

According to an embodiment, the electronic device may execute operation 1320 when identifying a change in the wearing state of the electronic device after performing operation 1315.

For example, the electronic device may identify the change in the wearing state of the electronic device using the sensor module. For example, the electronic device may identify the change in the wearing state of the electronic device using a rotary encoder (e.g., the rotary encoder 443) included in an actuator module (e.g., the actuator module 440). For example, the electronic device may identify the change in the wearing state of the electronic device based on the measurement of the rotational angle of the rotary encoder.

In operation 1325, the electronic device may determine a second signal value of the PPG signal measured during the specified period of time.

According to an embodiment, the second signal value may include a first parameter or a ratio of a first parameter to a second parameter. For example, the first parameter may include an AC signal value of the PPG signal, and the second parameter may include a DC signal value of the PPG signal.

In operation 1330, the electronic device may identify whether or not the second signal value is less than the first signal value.

According to an embodiment, if the second signal value is less than the first signal value in operation 1330, the electronic device may perform operation 1335. Otherwise, the electronic device may perform operation 1315.

In operation 1335, the electronic device may automatically change the wearing state of the electronic device on the user's body to be as loose as a specified reference.

According to an embodiment, the electronic device may include a first fastener (e.g., the first fastener 450) and a second fastener (e.g., the second fastener 460), and the first fastener may be moved in a second direction (e.g., the second direction 495) by a motor (e.g., the motor 441) of the electronic device while being coupled to the second fastener.

For example, the electronic device may move the first fastener in the second direction by the specified distance. According to the movement of the first fastener in the second direction, the degree of tightening of the electronic device worn on a body part of the user with respect to the body part of the user is further reduced, thereby increasing the distance between the electronic device and the body part of the user corresponding to the specific distance.

According to an embodiment, the electronic device may provide information indicating that the wearing state of the electronic device is to be automatically adjusted before operation 1335 and/or may provide information indicating that the wearing state of the electronic device is being automatically adjusted at the same time as operation 1335 through a display and/or a speaker.

In operation 1340, the electronic device may measure a PPG signal through the PPG sensor for a specified period of time.

According to an embodiment, the electronic device may execute operation 1340 when identifying a change in the wearing state of the electronic device after performing operation 1335.

For example, the electronic device may identify the change in the wearing state of the electronic device using the sensor module. For example, the electronic device may identify the change in the wearing state of the electronic device using a rotary encoder (e.g., the rotary encoder 443) included in an actuator module (e.g., the actuator module 440). For example, the electronic device may identify the change in the wearing state of the electronic device, based on the measurement of the rotational angle of the rotary encoder.

In operation 1345, the electronic device may determine a third signal value of the PPG signal measured for the specified period of time.

According to an embodiment, the third signal value may include a first parameter or a ratio of a first parameter to a second parameter. For example, the first parameter may include an AC signal value of the PPG signal, and the second parameter may include a DC signal value of the PPG signal.

In operation 1350, the electronic device may determine whether or not the third signal value is greater than the second signal value.

According to an embodiment, if the ratio of an AC signal value to a DC signal value, which is calculated the third time, is greater than the ratio of an AC signal value to a DC signal value, which is calculated the second time, in operation 1350, the electronic device may perform operation 1355. Otherwise, the electronic device may perform operation 1315.

In operation 1355, the electronic devices may identify biometric information.

According to an embodiment, the electronic device may identify the biometric information of the electronic device, based on the third signal value.

According to an embodiment, the electronic device may store the identified biometric information in the memory thereof.

In operation 1360, the electronic device may provide the identified biometric information.

According to an embodiment, the electronic device may provide the identified biometric information via a touch screen display and/or a speaker.

According to an embodiment, while the electronic device performs operations 1305 to 1360 in the embodiments shown in FIGS. 13A and 13B above, if one of the operations takes time exceeding the specified period of time, the electronic device may provide an error message to the user via the touch screen display and/or the speaker and may terminate the operations.

According to FIGS. 13A and 13B described above, the electronic device may calculate the signal value of the PPG sensor, which was initially measured, for a specified period of time, may then automatically adjust the distance between the electronic device and a body part of the user such that the straps of the electronic device come into tighter contact with the users skin, may measure a signal value of the PPG signal again for a specified period of time, and may compare the same with a previously measured value. If the subsequently measured signal value is greater than the previously measured signal value as a result of the comparison, the terminal may automatically adjust the degree of contact such that the straps come into tighter contact with a body part of the user, and if the subsequently measured signal value is less than the previously measured signal value, the terminal may adjust the degree of contact such that the straps come into looser contact with a body part of the user. The electronic device may repeat the operation of adjusting the degree of contact, so that the electronic device may reach an optimal contact state with the users skin. The electronic device may store, in the memory, the optimal distance between the electronic device and a body part of the user (i.e., the degree of contact between the electronic device and the users skin) after completing the measurement of the biometric information. When performing the above-described operation, if it takes more time than necessary to reach the optimized skin contact state, the electronic device may display an error message on the screen.

Figure 14A:
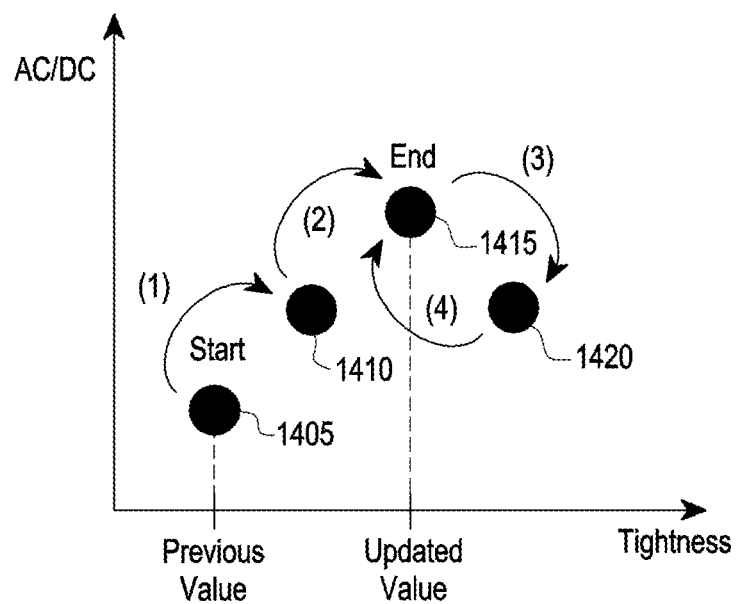
FIG. 14A illustrates a diagram of an operation of searching for a contact state between an electronic device and a users skin in order to measure optimal biometric information according to various embodiments.
Figure 14B:
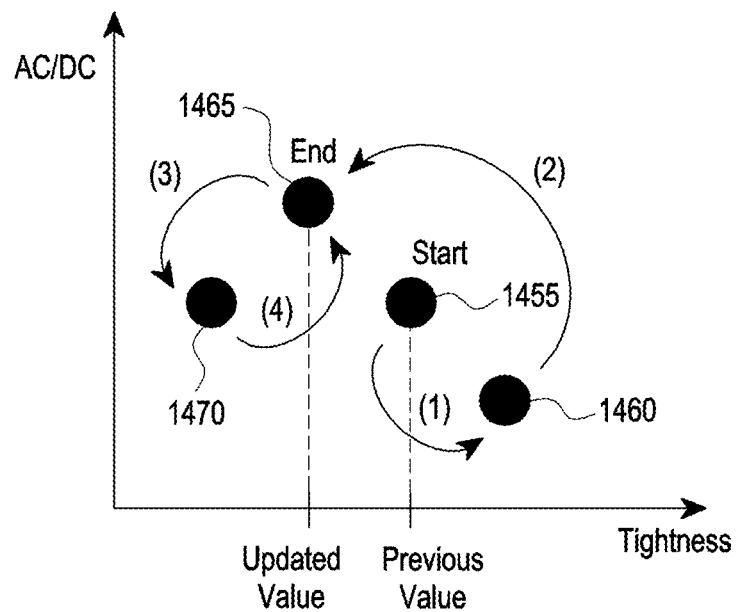
FIG. 14B illustrates a diagram of an operation of searching for a contact state between an electronic device and a users skin in order to measure optimal biometric information according to various embodiments.

FIG. 14A illustrates a diagram of an operation of searching for a contact state between an electronic device (e.g., the electronic device 101, the electronic device 201, or the electronic device 401) and a users skin in order to measure optimal biometric information according to various embodiments, and FIG. 14B illustrates a diagram of an operation of searching for a contact state between an electronic device (e.g., the electronic device 101, the electronic device 201, or the electronic device 401) and a users skin in order to measure optimal biometric information according to various embodiments.

Referring to FIGS. 14A and 14B, the electronic device may measure a PPG signal, and, based on the ratio of an AC signal value to a DC signal value of the PPG signal, the contact state between the electronic device and the users skin (the wearing state of the electronic device) may be adjusted manually by the user or automatically by the electronic device.

For example, when the electronic device measures a PPG signal of the same user, the ratio of an AC signal value to a DC signal value (and/or the AC amplitude value) of the PPG signal may differ due to variation in the physical condition of the user at the time of measurement. Thus, it may be required to change the distance between the electronic device and at least a part of the user's body (the contact state of the electronic device and the users skin) in order to measure optimal biometric information.

For example, according to the necessity to change the distance between the electronic device and at least a part of the user's body, based on the wearing state corresponding to a reference value stored in the memory (e.g., the memory 130 or the memory 280), the electronic device may re-perform an operation of determining an optimal wearing state of the electronic device (a searching operation).

For example, if the wearing state corresponding to the reference value stored in the memory of the electronic device according to the previous measuring operation is looser than the current wearing state, the electronic device may perform a searching operation as shown in FIG. 14A and may update the reference with a final value. For example, if the wearing state corresponding to the reference value stored in the memory of the electronic device according to the previous measuring operation is tighter than the current wearing state, the electronic device may perform a searching operation as shown in FIG. 14B and may update the reference with a final value.

Referring to FIG. 14A, the electronic device may measure a first PPG signal while being worn on the user and may obtain a first signal value 1405, which is the ratio of an AC signal value to a DC signal value of the first PPG signal. For example, after the wearing state of the electronic device is adjusted to be as tight as a specified value manually by the user or automatically by the electronic device, the electronic device may measure a second PPG signal.

If a second value 1410, which is the ratio of an AC signal value to a DC signal value of the measured second PPG signal, is greater than the first value 1405, the wearing state of the electronic device may be adjusted to be as tight as a specified value manually by the user or automatically by the electronic device. Thereafter, the electronic device may measure a third PPG signal.

If a third value 1415, which is the ratio of an AC signal value to a DC signal value of the measured third PPG signal, is greater than the second value 1410, the wearing state of the electronic device may be adjusted to be as tight as a specified value manually by the user or automatically by the electronic device. Thereafter, the electronic device may measure a fourth PPG signal.

If a fourth value 1420, which is the ratio of an AC signal value to a DC signal value of the measured fourth PPG signal, is less than the third value 1415, the electronic device may stop measuring the PPG signal and may determine the third value 1415 to be an optimal wearing state value, thereby storing the same as a reference value. Based on the determination of the third value 1415 as the optimal wearing state value, the user may manually adjust the wearing state of the electronic device to the state corresponding to the third value 1415 or the electronic device may automatically adjust the wearing state of the electronic device to the state corresponding to the third value 1415.

According to an embodiment, the first value 1405 to the fourth value 1420 may be the ratios of AC signal values to DC signal values of the PPG signals measured in a loose state (e.g., the fourth contact state 1120), a normal state (e.g., the third contact state 1115), a tight state (e.g., the second contact state 1110), and a tightest state (e.g., the first contact state 1105), respectively.

Referring to FIG. 14B, the electronic device may measure a first PPG signal while being worn on the user and may obtain a fifth signal value 1455, which is the ratio of an AC signal value to a DC signal value of the PPG signal. For example, after the wearing state of the electronic device is adjusted to be as tight as a specified value manually by the user or automatically by the electronic device, the electronic device may measure a second PPG signal.

If a sixth value 1460, which is the ratio of an AC signal value to a DC signal value of the measured second PPG signal, is less than the fifth value 1455, the wearing state of the electronic device may be adjusted to be as loose as a specified value manually by the user or automatically by the electronic device. Thereafter, the electronic device may measure a third PPG signal.

If a seventh value 1465, which is the ratio of an AC signal value to a DC signal value of the measured third PPG signal, is greater than the fifth value 1455 and the sixth value 1460, the wearing state of the electronic device may be adjusted to be as loose as a specified value manually by the user or automatically by the electronic device. Thereafter, the electronic device may measure a fourth PPG signal.

If an eighth value 1470, which is the ratio of an AC signal value to a DC signal value of the measured fourth PPG signal, is less than the seventh value 1465, the electronic device may stop measuring the PPG signal and may determine the seventh value 1465 to be an optimal wearing state value. Based on the determination of the seventh value 1465 as the optimal wearing state value, the user may manually adjust the wearing state of the electronic device to the state corresponding to the seventh value 1465, or the electronic device may automatically adjust the wearing state of the electronic device to the state corresponding to the seventh value 1465.

In connection with the embodiments in FIGS. 8, 13A, 13B, 14A, and/or 14B, it has been described that the electronic device (e.g. the electronic device 101, the electronic device 201, or the electronic device 401) performs control such that the first fastener of the electronic device is moved in the first direction or the second direction by a specified distance using the motor of the electronic device so as to automatically perform adjustment to increase or reduce the distance between the electronic device and a body part of the user. Although not shown, according to another embodiment, the electronic device (e.g., the electronic device 101, the electronic device 201, or the electronic device 401) may perform control such that the volume of the second portion (e.g., the second portion 410b) of the housing (e.g., the housing 410) of the electronic device is automatically adjusted, thereby automatically performing adjustment to increase or reduce the distance between the electronic device and a body part of the user. For example, if the distance between the electronic device and a body part of the user is greater than a stored reference distance, the electronic device may increase the volume of the second portion of the electronic device by a specified amount. According to the expansion in the volume, the distance between the electronic device and a body part of the user may be reduced. For example, if the distance between the electronic device and a body part of the user is less than a stored reference distance, the electronic device may reduce the volume of the second portion of the electronic device by a specified amount. According to the reduction in the volume, the distance between the electronic device and a body part of the user may be increased.

Figure 15A:
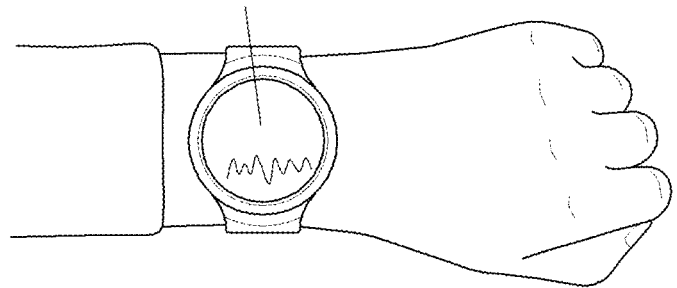
FIG. 15A illustrates a diagram of a wearing guidance screen of an electronic device according to various embodiments.
Figure 15B:
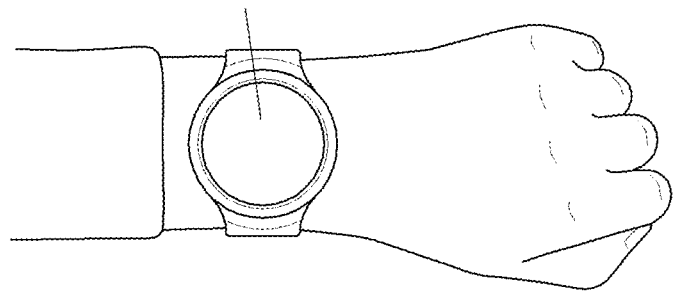
FIG. 15B illustrates a diagram of a wearing guidance screen of an electronic device according to various embodiments.
Figure 15C:
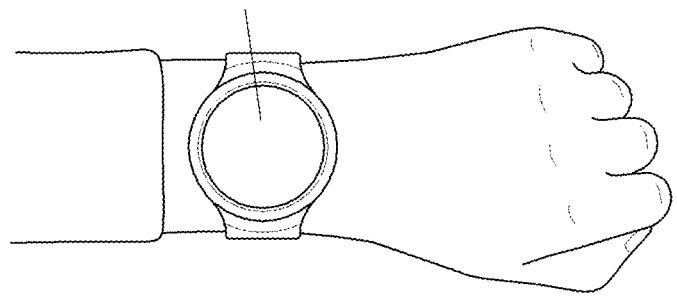
FIG. 15C illustrates a diagram of a wearing guidance screen of an electronic device according to various embodiments.

FIG. 15A illustrates a diagram of a wearing guidance screen of an electronic device according to various embodiments. FIG. 15B illustrates a diagram of a wearing guidance screen of an electronic device according to various embodiments. FIG. 15C illustrates a diagram of a wearing guidance screen of an electronic device according to various embodiments.

According to an embodiment, when the electronic device (e.g., the electronic device 101, the electronic device 201, or the electronic device 401) measures a PPG signal and/or determines a signal value of the measured PPG signal, the electronic device may display information stating that biometric information is being checked on the touch screen display. The information stating that biometric information is being checked may include a phrase such as "Checking accuracy of biometric signal" as shown in FIG. 15A.

According to an embodiment, when the electronic device provides wearing guidance information, the electronic device may display the wearing guidance information on the touch screen display. For example, the electronic device may provide information on the number of holes on the straps, thereby allowing the user to adjust the degree of tightening. The wearing guidance information may include a phrase such as "Please tighten your straps one more pitch!" as shown in FIG. 15B.

According to an embodiment, when the electronic device automatically adjusts the wearing state of the electronic device, the electronic device may provide guidance information to the touch screen display. The guidance information may include a phrase such as "Tightness is adjusted for accurate measurement" as shown in FIG. 15C.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wired), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturers server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various embodiments, a storage medium may include instructions that, when executed by at least one circuit, allow the at least one circuit to perform one or more operations of: receiving data from a photoplethysmogram sensor of the electronic device; based at least in part on the received data, determining a first parameter; based at least in part on the determined first parameter, determining a distance between a body part of the user and a fastening structure of the electronic device; and based at least in part on the distance, providing user guidance information on the display of the electronic device.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device comprising:
a housing;
a display configured to be viewed through a first portion of the housing;
a photoplethysmogram (PPG) sensor exposed through a second portion of the housing and configured to measure a biometric signal from a body part of a user while being in contact with the body part of the user;
a fastening structure connected to a portion of the housing and configured to be attached to the body part of the user;
a wireless communication circuit;
a processor disposed inside the housing and operatively connected to the display, the PPG sensor, and the wireless communication circuit; and
a memory operatively connected to the processor,
wherein the memory stores instructions that when executed, are configured to cause the processor to:
activate the PPG sensor and measure light-emitting diode (LED) signals using at least one LED included in the PPG sensor,
based on the measured LED signals, determine whether or not the electronic device is in contact with the body part of the user,
in response to determine that the electronic device is in contact with the body part of the user, provide first user guidance information on the display, the first user guidance information guiding a specified wearing position in which the electronic device should be located on the body part of the user,
determine whether or not a current wearing position of the electronic device is the specified wearing position,
in response to determine that the current wearing position of the electronic device is the specified wearing position, receive data from the PPG sensor,
based at least in part on the received data from the PPG sensor, determine a first parameter,
based at least in part on the determined first parameter, determine a distance between the body part of the user and the fastening structure, and
based at least in part on the distance, provide second user guidance information on the display.

2. The electronic device of claim 1, wherein the instructions cause the processor to:
based at least in part on the received data from the PPG sensor, determine a second parameter; and
based at least in part on the determined first parameter and the determined second parameter, determine the distance.

3. The electronic device of claim 2, wherein the instructions cause the processor to:
based at least in part on a ratio of the determined first parameter to the determined second parameter, determine the distance.

4. The electronic device of claim 3, wherein:
the PPG sensor comprises a light-receiving module comprising the at least one LED and at least one photodiode;
the first parameter comprises information on an amount of light that is emitted from the LED, passes through a blood vessel of the user, and is reflected thereby to then be received by the light-receiving module; and
the second parameter comprises information on an amount of light that is emitted from the LED, passes through a living tissue other than the blood vessel of the user, and is reflected thereby to then be received by the light-receiving module.

5. The electronic device of claim 1, wherein:
the fastening structure further comprises an actuator module; and
the instructions cause the processor to, based at least in part on the determined first parameter, adjust the distance between the body part and the fastening structure using the actuator module.

6. The electronic device of claim 5, wherein the instructions cause the processor to, if the distance is less than a reference distance stored in the memory, perform adjustment to increase the distance between the body part and the fastening structure by a specified reference value using the actuator module.

7. The electronic device of claim 5, wherein the instructions cause the processor to, if the distance is greater than a reference distance stored in the memory, perform adjustment to reduce the distance between the body part and the fastening structure by a specified reference value using the actuator module.

8. The electronic device of claim 1, wherein the electronic device is a wearable device.

9. The electronic device of claim 1, further comprising:
a motion sensor module,
wherein the instructions cause the processor to:
obtain at least one acceleration value through the motion sensor module, and
wherein determine whether or not the current wearing position of the electronic device is the specified wearing position is performed based at least in part on the obtained acceleration value.

10. The electronic device of claim 1, further comprising:
a sensor module,
wherein the instructions cause the processor to:
based on at least one piece of schedule information stored in the memory, location information of the electronic device obtained through the sensor module, acceleration information of the electronic device obtained through the sensor module, or current time information, identify status information of the electronic device, and
based at least in part on the status information of the electronic device, activate the PPG sensor.

11. A method for detecting biometric information in an electronic device, the method comprising:
activating a photoplethysmogram (PPG) sensor;
measuring light-emitting diode (LED) signals using at least one LED included in the PPG sensor;
based on the measured LED signals, determining whether or not the electronic device is in contact with a body part of a user;
in response to determine that the electronic device is in contact with the body part of the user, providing first user guidance information on a display, the first user guidance information guiding a specified wearing position in which the electronic device should be located on the body part of the user;
determining whether or not a current wearing position of the electronic device is the specified wearing position;
in response to determine that the current wearing position of the electronic device is the specified wearing position, receiving data from the PPG sensor of the electronic device;
based at least in part on the received data, determining a first parameter;
based at least in part on the determined first parameter, determining a distance between a body part of a user and a fastening structure of the electronic device; and
based at least in part on the distance, providing second user guidance information on the display of the electronic device.

12. The method of claim 11, wherein the determining the distance between the body part of the user and the fastening structure of the electronic device comprises:
based at least in part on the received data, determining a second parameter; and
based at least in part on the determined first parameter and the determined second parameter, determining the distance.

13. The method of claim 12, wherein the determining the distance between the body part of the user and the fastening structure of the electronic device comprises, based at least in part on a ratio of the determined first parameter to the determined second parameter, determining the distance.

14. The method of claim 13, wherein:
the PPG sensor comprises a light-receiving module comprising the at least LED and at least one photodiode;
the first parameter comprises information on an amount of light that is emitted from the LED, passes through a blood vessel of the user, and is reflected thereby to then be received by the light-receiving module; and
the second parameter comprises information on an amount of light that is emitted from the LED, passes through a living tissue other than the blood vessel of the user, and is reflected thereby to then be received by the light-receiving module.

15. The method of claim 11, further comprising, based at least in part on the determined first parameter, adjusting the distance between the body part and the fastening structure of the electronic device using an actuator module of the electronic device.

16. The method of claim 15, further comprising, if the distance is less than a reference distance stored in a memory of the electronic device, performing an adjustment to increase the distance between the body part and the fastening structure of the electronic device by a specified reference value using the actuator module of the electronic device.

17. The method of claim 15, further comprising, if the distance is greater than a reference distance stored in a memory of the electronic device, performing an adjustment to reduce the distance between the body part and the fastening structure of the electronic device by a specified reference value using the actuator module of the electronic device.

18. An electronic device comprising:
a housing;
a display configured to be viewed through a first portion of the housing;
a photoplethysmogram (PPG) sensor configured to be exposed through a second portion of the housing and configured to measure a biometric signal from a body part of a user while being in contact with the body part of the user;
a fastening structure connected to a portion of the housing and configured to be attached to the body part of the user;
a wireless communication circuit;
a processor disposed inside the housing and operatively connected to the display, the PPG sensor, and the wireless communication circuit; and
a memory operatively connected to the processor,
wherein the memory stores instructions that when executed, are configured to cause the processor to:
activate the PPG sensor and measure light-emitting diode (LED) signals using at least one LED included in the PPG sensor,
based on the measured LED signals, determine whether or not the electronic device is in contact with the body part of the user,
in response to determine that the electronic device is in contact with the body part of the user, provide first user guidance information on the display, the first user guidance information guiding a specified wearing position in which the electronic device should be located on the body part of the user,
determine whether or not a current wearing position of the electronic device is the specified wearing position,
in response to determine that the current wearing position of the electronic device is the specified wearing position, receive data from the PPG sensor, based at least in part on the received data, determine a first parameter,
based at least in part on the determined first parameter, determine a degree of contact between the body part of the user and the fastening structure, and
based at least in part on the degree of contact, provide user guidance information on the display.

19. The electronic device of claim 18, wherein the instructions cause the processor to determine the degree of contact according to at least one of a distance between the body part of the user and the fastening structure or a pressure applied to the body part of the user by the fastening structure.

* * * * *